(12) United States Patent
Maloney et al.

(10) Patent No.: US 7,413,846 B2
(45) Date of Patent: Aug. 19, 2008

(54) FABRICATION METHODS AND STRUCTURES FOR MICRO-RESERVOIR DEVICES

(75) Inventors: John M. Maloney, Cambridge, MA (US); Zouhair Sbiaa, Malden, MA (US); John T. Santini, Jr., North Chelmsford, MA (US); Norman F. Sheppard, Jr., Bedford, MA (US); Scott A. Uhland, Roslindale, MA (US)

(73) Assignee: MicroCHIPS, Inc., Bedford, MA (US)

( * ) Notice: Subject to any disclaimer, the term of this patent is extended or adjusted under 35 U.S.C. 154(b) by 485 days.

(21) Appl. No.: 10/988,667

(22) Filed: Nov. 15, 2004

(65) Prior Publication Data
US 2006/0105275 A1    May 18, 2006

(51) Int. Cl.
*G03F 7/20* (2006.01)
(52) U.S. Cl. .................. 430/320; 430/322; 430/323
(58) Field of Classification Search ................. 430/320, 430/318, 323, 322
See application file for complete search history.

(56) References Cited

U.S. PATENT DOCUMENTS

| | | | |
|---|---|---|---|
| 4,089,734 A | 5/1978 | Bierig | |
| 4,209,894 A | 7/1980 | Keen | |
| 4,345,981 A | 8/1982 | Bennett et al. | |
| 4,734,300 A | 3/1988 | Simanyi et al. | |
| 4,793,825 A | 12/1988 | Benjamin et al. | |
| 5,042,975 A | 8/1991 | Chien et al. | |
| 5,167,625 A | 12/1992 | Jacobsen et al. | |
| 5,200,051 A | 4/1993 | Cozzette et al. | |
| 5,252,294 A | 10/1993 | Kroy et al. | |
| 5,262,127 A | 11/1993 | Wise et al. | |
| 5,304,293 A | 4/1994 | Tierney et al. | |
| 5,324,316 A | 6/1994 | Schulman et al. | |
| 5,336,213 A | 8/1994 | D'Angelo et al. | |

(Continued)

FOREIGN PATENT DOCUMENTS

DE    197 16 683 C1    6/1998

(Continued)

OTHER PUBLICATIONS

Becker, et al., *Sensors & Actuators* 83: 130-35 (2000).

(Continued)

*Primary Examiner*—Mark F. Huff
*Assistant Examiner*—Brittany Raymond
(74) *Attorney, Agent, or Firm*—Sutherland Asbill & Brennan LLP; Edward S. Podszus

(57) ABSTRACT

Methods are provided for making a multi-reservoir device comprising (i) patterning one or more photoresist layers on a substrate; (ii) depositing onto the substrate at least one metal layer by a sputtering process to form a plurality of reservoir caps and conductive traces; (iii) removing the photoresist layers using a liftoff process; (iv) forming a plurality of reservoirs in the substrate; (v) loading each reservoir with reservoir contents (such as a drug or sensor); and (vi) sealing each reservoir. Optionally, the reservoir cap comprises a first conductive metal layer coated with one or more protective noble metal films. To enhance the resistance of the substrate (e.g., a silicon substrate) to etching in vivo, the interior sidewalls of the reservoirs optionally can include a protective coating (e.g., gold, platinum, carbon, silicon carbide, silicon dioxide, and platinum silicide), or sidewalls comprising silicon can be doped with boron or another impurity.

32 Claims, 14 Drawing Sheets

U.S. PATENT DOCUMENTS

| | | | |
|---|---|---|---|
| 5,366,454 | A | 11/1994 | Currie et al. |
| 5,368,588 | A | 11/1994 | Bettinger |
| 5,368,704 | A | 11/1994 | Madou et al. |
| 5,385,709 | A | 1/1995 | Wise et al. |
| 5,427,585 | A | 6/1995 | Bettinger |
| 5,474,527 | A | 12/1995 | Bettinger |
| 5,490,962 | A | 2/1996 | Cima et al. |
| 5,510,138 | A | 4/1996 | Sanftleben et al. |
| 5,524,338 | A | 6/1996 | Martyniuk et al. |
| 5,533,995 | A | 7/1996 | Corish et al. |
| 5,605,662 | A | 2/1997 | Heller et al. |
| 5,651,900 | A | 7/1997 | Keller et al. |
| 5,660,680 | A | 8/1997 | Keller |
| 5,770,076 | A | 6/1998 | Chu et al. |
| 5,782,799 | A | 7/1998 | Jacobsen et al. |
| 5,797,898 | A | 8/1998 | Santini, Jr. et al. |
| 5,824,204 | A | 10/1998 | Jerman |
| 5,843,767 | A | 12/1998 | Beattie |
| 5,893,974 | A | 4/1999 | Keller et al. |
| 5,900,160 | A | 5/1999 | Whitesides et al. |
| 5,925,069 | A | 7/1999 | Graves et al. |
| 5,938,923 | A | 8/1999 | Tu et al. |
| 5,962,081 | A | 10/1999 | Ohman et al. |
| 5,976,101 | A | 11/1999 | Sibalis |
| 5,989,445 | A | 11/1999 | Wise et al. |
| 6,042,710 | A | 3/2000 | Dubrow |
| 6,062,461 | A * | 5/2000 | Sparks et al. ............. 228/123.1 |
| 6,096,656 | A | 8/2000 | Matzke et al. |
| 6,114,658 | A | 9/2000 | Roth et al. |
| 6,123,861 | A | 9/2000 | Santini, Jr. et al. |
| 6,136,212 | A | 10/2000 | Mastrangelo et al. |
| 6,163,720 | A | 12/2000 | Gyory et al. |
| 6,232,150 | B1 | 5/2001 | Lin et al. |
| 6,349,232 | B1 | 2/2002 | Gordon |
| 6,436,853 | B2 | 8/2002 | Lin et al. |
| 6,483,368 | B2 | 11/2002 | Mayer et al. |
| 6,491,666 | B1 | 12/2002 | Santini, Jr. et al. |
| 6,527,762 | B1 * | 3/2003 | Santini et al. ............. 604/890.1 |
| 6,534,247 | B2 * | 3/2003 | Milligan et al. ............. 430/320 |
| 6,537,256 | B2 | 3/2003 | Santini, Jr. et al. |
| 6,551,838 | B2 | 4/2003 | Santini, Jr. et al. |
| 6,571,125 | B2 | 5/2003 | Thompson |
| 6,656,162 | B2 | 12/2003 | Santini, Jr. et al. |
| 6,663,615 | B1 | 12/2003 | Madou et al. |
| 6,669,683 | B2 | 12/2003 | Santini, Jr. et al. |
| 6,730,072 | B2 | 5/2004 | Shawgo et al. |
| 6,773,429 | B2 | 8/2004 | Sheppard, Jr. et al. |
| 6,808,522 | B2 | 10/2004 | Richards et al. |
| 6,827,250 | B2 | 12/2004 | Uhland et al. |
| 6,849,463 | B2 | 2/2005 | Santini, Jr. et al. |
| 6,903,433 | B1 * | 6/2005 | McFarland et al. ........... 257/471 |
| 2001/0010885 | A1 * | 8/2001 | Kamijima ..................... 430/15 |
| 2002/0072734 | A1 | 6/2002 | Liedtke |
| 2002/0072784 | A1 | 6/2002 | Sheppard, Jr. et al. |
| 2002/0099359 | A1 | 7/2002 | Santini, Jr. et al. |
| 2002/0111658 | A1 | 8/2002 | Greenberg et al. |
| 2002/0119176 | A1 | 8/2002 | Greenberg et al. |
| 2002/0183721 | A1 | 12/2002 | Santini, Jr. et al. |
| 2002/0187260 | A1 | 12/2002 | Sheppard, Jr. et al. |
| 2002/0189078 | A1 * | 12/2002 | Lu et al. .................. 29/603.15 |
| 2003/0032946 | A1 | 2/2003 | Fishman |
| 2003/0055344 | A1 | 3/2003 | Eigler et al. |
| 2003/0069560 | A1 | 4/2003 | Adamis et al. |
| 2003/0178403 | A1 | 9/2003 | Lemmerhirt et al. |
| 2004/0043042 | A1 | 3/2004 | Johnson et al. |
| 2004/0082937 | A1 | 4/2004 | Ausiello et al. |
| 2004/0106914 | A1 | 6/2004 | Coppeta et al. |
| 2004/0106953 | A1 * | 6/2004 | Yomtov et al. .................. 607/3 |
| 2004/0121486 | A1 | 6/2004 | Uhland et al. |
| 2004/0127942 | A1 | 7/2004 | Yomtov et al. |
| 2004/0166140 | A1 | 8/2004 | Santini, Jr. et al. |
| 2004/0247671 | A1 | 12/2004 | Prescott, et al. |
| 2004/0248320 | A1 | 12/2004 | Santini, Jr. et al. |
| 2005/0050859 | A1 | 3/2005 | Coppeta et al. |
| 2005/0055014 | A1 | 3/2005 | Coppeta et al. |

FOREIGN PATENT DOCUMENTS

| | | |
|---|---|---|
| EP | 0341843 A | 11/1989 |
| EP | 0 347 579 B1 | 3/1994 |
| WO | WO02/056862 A1 | 7/2002 |
| WO | 03078874 A | 9/2003 |

OTHER PUBLICATIONS

Becker, et al., *J. Micromech. Microeng.* 8: 24-28 (1998).

Becker, et al. in *Microfluidic devices and Systems III* (Mastrangelo, et al., eds.) Proc. of SPIE, vol. 4177 (2000).

Laermer, et al., 12$^{th}$ IEEE Intl. Conf. MEMS (Jan. 1999).

Madou, et al., "From Batch to Continuous Manufacturing of Microbiomedical Devices," *Chem Rev.* 100: 2679-92 (2000).

Madou, et al., "Exploitation of a Novel Artificial Muscle for Controlled Drug Delivery," *Polym. Mater. Sci. Eng.* 83: 495-497 (2000).

Santini, et al., *Angew Chem. Int. Ed. Engl.* 39(14): 2396-407 (2000).

Santini, et al., *Ann. Med.* 32(6) 377-79 (2001) (abstract).

Santini, et al., *Nature* 397(6717): 335-38 (1999).

Surbled, et al., "Shape Memory Alloys for Micromembranes Actuation," *SPIE* 3825: 63-70 (1999).

Surbled, et al., "Array of Shape Memory Alloy One-Shot Micro-Valves for Drug Delivery", MME '99, Gif sur Yvette, France (Sep. 27-28, 1999).

Surbled, et al., *Jpn. J. Applied Phys.* 38: L1547-49 (1999).

Tierney, et al., "Electroreleasing Composite Membranes For Delivery of Insulin and Other Biomacromolecules," *J. Electrochem Soc.* 137(6): 2005-06 (1990).

Tierney, et al., "New Electrorelease Systems Based on Microporous Membranes," *J. Electrochem. Soc.* 137(12): 3789-93 (1990).

"LOR Lift-Off Resists," *Micro-Chem Corp.* Manual. (2002).

Tixier A., et al., "A Silicon Shodaw Mask for Deposition on Isolated Areas," *J. Micromech. Microeng.* 10:157-162 (2000).

Burger, et al., "High-resolution shadow-mask patterning in deep holes and its application to an electrical wafer feed-through," *Sensors and Actuators*, 54:669-673 (1996).

Kim, et al., "All-photoplastic microstencil with self-alignment for multiple layer shadow-mask patterning," *Sensors and Actuators*, 107:132-126 (2003).

Tixier, et al., "A Silicon Shadow Mask for Deposition on Isolated Areas," *J. Micromech. Microeng*, 10:157-162 (2000).

Maloney, et al., International Search Report of the International Searching Authority, PCT/US2005/041453.

Diepold, et al., "Smoothing of ultrasonically drilled holes in borosilicate glass by wet chemical etching," J. Micromech. Microeng. 6: 29-32 (1996).

Visser, et al., "Sodium distribution in thin-film anodic bonding," Sensors and Actuators A 92: 223-228 (2001).

Williams, et al., "Etch Rates for Micromachining Processing—Part II," J. Microelectromech. Sys. 12(6): 761-778 (2003).

* cited by examiner

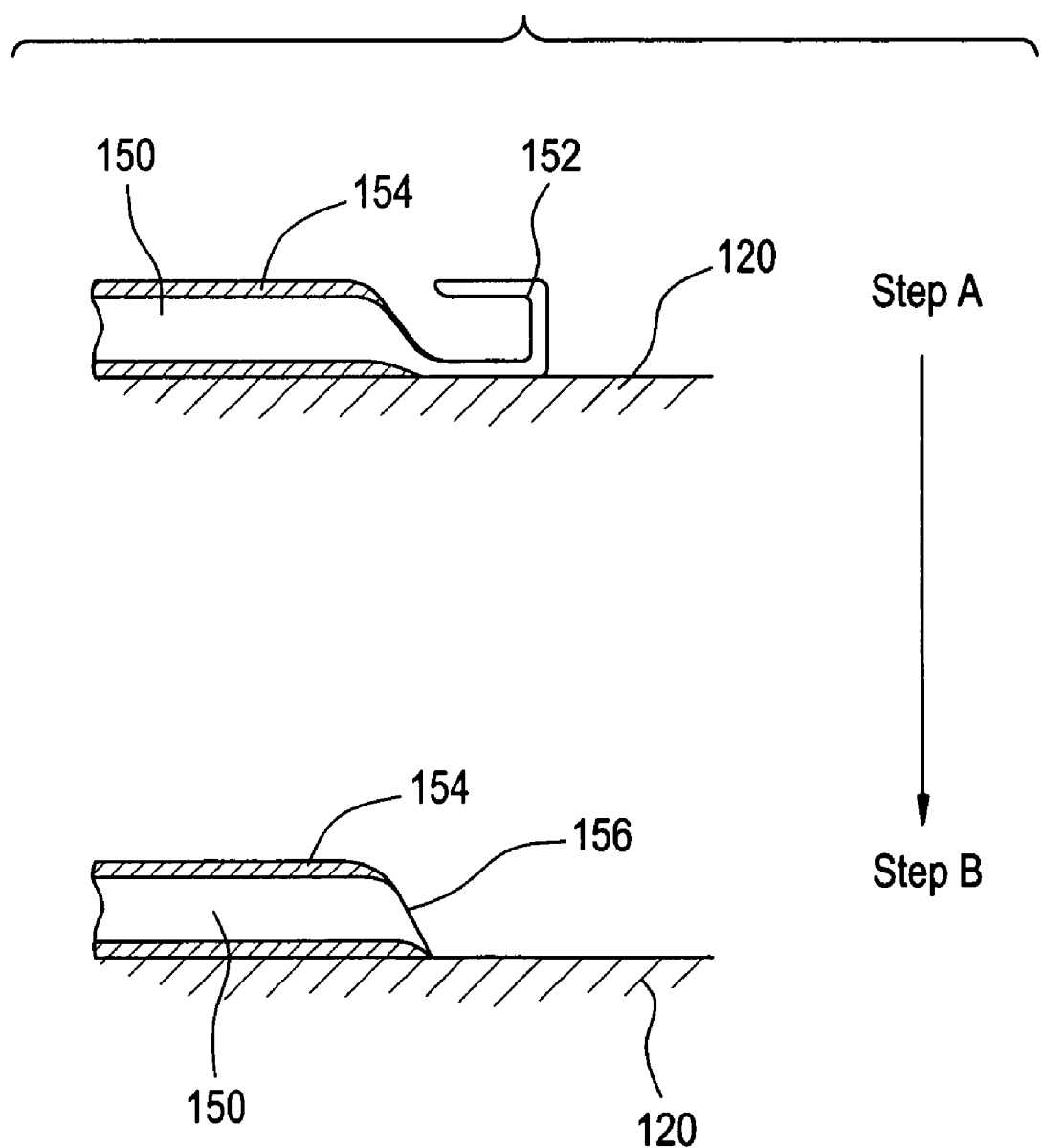

US 7,413,846 B2

FABRICATION METHODS AND STRUCTURES FOR MICRO-RESERVOIR DEVICES

BACKGROUND OF THE INVENTION

This invention is generally in the field of methods of fabricating miniaturized reservoir devices for the controlled release or exposure of reservoir contents, such as drug formulations and/or sensors.

U.S. Pat. No. 5,797,898, U.S. Pat. No. 6,551,838, and U.S. Pat. No. 6,491,666, all to Santini, et al., describe microfabricated devices that have a plurality, typically hundreds to thousands, of tiny reservoirs. In some embodiments, these reservoirs are provided with a reservoir cap over the contents (such as a drug formulation) of the reservoir, so that the contents are released from the device by the controllable disintegration of the reservoir caps. For example, the reservoir cap can be a metal film and an electric potential can be applied to cause the metal film to oxidize and disintegrate. In this embodiment, the microchip device is connected to an external circuit through wire bond pads on the microchip (i.e., on the substrate), and an electrical connection between the reservoir caps and the bond pads is provided by conductive traces fabricated on the chip. The reservoir caps, traces, and bond pads can be fabricated, for example, using a single patterned layer of gold.

U.S. patent application Publication No. 2004/0121486 A1 to Uhland, et al., also describes devices having an array of micro-reservoirs each covered by a reservoir cap. The publication further describes a innovative means for disintegrating the reservoir cap to expose/release the reservoir contents: An electrical current is selectively passed through each reservoir cap, via an input lead and an output lead, in an amount effective to heat the reservoir cap to cause the reservoir cap to rupture, thus opening the reservoir. One embodiment includes reservoir caps, traces, and bond pads fabricated from a conductive material. In one embodiment, the reservoir caps and traces are fabricated from different materials and are electrically connected. It would be desirable to provide devices and fabrication methods in which the surface of the exterior or interior of the device or the substrate can be coated or altered to protect the device from the environment or to obtain a favorable surface chemistry for drug storage. It would be further desirable to provide methods for fabricating multi-reservoir devices wherein the circuitry is fabricated in a robust manner and good physical and electrical contact is maintained between features of the device that are meant to be electrically connected.

U.S. Pat. No. 6,123,861 to Santini, et al., describes forming reservoirs in a substrate by etching a single crystal silicon wafer using aqueous potassium hydroxide. Because the pyramidal reservoirs formed by this process are defined by silicon crystalline planes, the area density of reservoirs on the wafer is inversely coupled to the volume of each reservoir.

It would be advantageous to have micro-reservoir devices that have a high area density in order to pack more reservoir contents into as small a total device volume as possible, particularly for applications where the device is to be implanted into a patient (such as for controlled drug delivery or biosensing). It therefore would be desirable to develop improved devices and new methods of making them in which the reservoir volume in these devices can be increased without adversely affecting the area density of reservoirs on/in a substrate.

BRIEF SUMMARY OF THE INVENTION

In one aspect, a method is provided for making a multi-reservoir device comprising the steps of (i) patterning one or more photoresist layers on a substrate; (ii) depositing onto the substrate at least one metal layer by physical vapor deposition; (iii) forming a plurality of reservoir caps and conductive traces from the at least one metal layer by using the one or more photoresist layers in a liftoff process or wet chemical etching (iv) removing the one or more photoresist layers using a liftoff process; (v) forming a plurality of reservoirs in the substrate; (vi) loading each reservoir with reservoir contents; and (vii) sealing each reservoir.

In one embodiment, the reservoir cap comprises a first conductive metal layer coated with one or more protective noble metal film layers. For example, the first conductive metal layer can comprise titanium, and the noble metal film can comprise platinum. In one embodiment, the thickness of the protective metal layer is less than about 20% of the thickness of the first conductive metal layer.

In another embodiment, the reservoirs comprise interior sidewalls and the method further includes forming a protective surface on the sidewalls. For example, a coating layer can be formed on the sidewalls, such as a material selected from gold, platinum, diamond-like carbon, silicon carbide, silicon dioxide, and platinum silicide. In an alternative approach, the reservoirs comprise interior sidewalls comprising silicon doped with boron or another impurity to enhance the resistance of the silicon to etching under in vivo conditions.

In one embodiment, the method further comprises bonding an additional substrate portion with through-substrate holes aligned with the reservoirs. For example, the additional substrate portion can comprise a silicon wafer or a glass wafer. In one embodiment, the additional substrate portion and the substrate are bonded together with an intermediate film, such as a borosilicate glass. In one embodiment, the substrate and/or the additional substrate portion comprises silicon and the reservoirs and/or through holes are further treated with an isotropic silicon etchant to widen the hole or to smooth the surface of the hole. In various embodiments, the additional substrate portion and the substrate are bonded by a process comprising anodic bonding, thermocompression bonding, or eutectic bonding.

In still another embodiment, the method includes a bilayer liftoff process. For instance, a bilayer photoresist which comprises an upper layer and a lower layer, can be deposited where the lower layer is disposed on the substrate and the upper layer is disposed on the lower layer. Preferably, the method provides a metal layer with no tags created by the sputtering and liftoff processes. For example, the lower layer can be laterally etched before the sputtering step, to create an overhang of the upper layer so that substantially no sputtered material is deposited on the sidewall of the lower layer. In an alternative embodiment, the process includes the formation of tags connected to the metal layer and the tags are then removed. In one example, the tags are removed by a process comprising: (i) depositing a mask layer is deposited over the metal traces and/or reservoir caps, wherein the mask layer: metal layer thickness ratio is from about 1:5 to about 1:1000; and (ii) etching away the tags to yield metal traces and/or reservoir caps. In another example, the tags are removed by a sonication process.

In one particular embodiment, a method is provided for making a multi-reservoir device comprising the steps of (i) depositing a layer of a nitride material on a silicon substrate; (ii) patterning the nitride layer with photoresist; (iii) etching the silicon substrate using an RIE process; (iii) stripping off the photoresist; (iv) anistropically etching the silicon silicon substrate; (v) forming metal traces by depositing and patterning a first metal layer using a liftoff technique; (vi) forming reservoir caps by depositing and patterning a second metal layer using a liftoff technique to form a structure; (vii) applying a passivation layer onto the structure; and (viii) etching the dielectric layer and the metal layer from under the reservoir cap. In a further embodiment, the method further includes anodically bonding a patterned glass wafer to the substrate.

In another aspect, a microfabrication method is provided comprising the steps of (i) patterning a bilayer of photoresist on a substrate, wherein the bilayer photoresist comprises an upper layer and a lower layer, the lower layer being disposed on top of the substrate and the upper layer being disposed on top of the lower layer; (ii) etching the lower layer away in select areas to form one or more bridges comprising areas of the upper layer over and spaced apart from the substrate; (iii) depositing onto the substrate at least one metal layer by physical vapor deposition, wherein the one or more bridges provide a shielding effect to produce a metal film or patterned metal feature with a thickness variation within a single metal layer, without etching the metal layer. In one embodiment, the method further comprises (iv) forming a plurality of reservoir caps and conductive traces from the at least one metal layer by using the one or more photoresist layers in a liftoff process or wet chemical etching; (v) removing the bilayer photoresist layers using a liftoff process; (vi) forming a plurality of reservoirs in the substrate; (vii) loading each reservoir with reservoir contents; and (viii) sealing each reservoir, wherein the thickness of the metal layer is varied due to a shielding effect caused by the bridges. In various embodiments, the method of depositing the metal layer is selected from evaporation, sputtering, and ion beam deposition.

In preferred embodiments of these methods, the reservoirs are micro-reservoirs, the reservoir contents comprises one or more drugs, the reservoir contents comprises one or more sensors or sensor components, and/or the reservoir contents are hermetically sealed within the reservoirs.

In another aspect, an implantable medical device is provided for the controlled delivery or exposure of reservoir contents. The device comprises (i) a substrate; (ii) a plurality of discrete reservoirs in the substrate, wherein the reservoirs have interior walls and at least one opening in the substrate; (iii) reservoir contents disposed in the reservoirs; (iv) reservoir caps closing the at least one opening to seal the reservoir contents in the reservoirs; and (v) control circuitry for selectively disintegrating the reservoir caps to release or expose the reservoir contents in vivo, wherein the interior walls of the reservoirs comprise a material to protect the substrate in vivo. In one embodiment, the interior sidewalls have at least one protective layer of the material coated thereon. For example, the protective layer can comprise gold, platinum, diamond-like carbon, silicon carbide, silicon dioxide, or platinum silicide. In another embodiment, the interior sidewalls comprise silicon doped with boron or another impurity to enhance the resistance of the silicon to etching in vivo.

In another aspect, an implantable medical device is provided for the controlled delivery or exposure of reservoir contents. The device comprises (i) a substrate; (ii) a plurality of reservoirs in the substrate, wherein the reservoirs have interior walls and at least one opening in the substrate; (iii) reservoir contents disposed in the reservoirs; (iv) reservoir caps closing the at least one opening to seal the reservoir contents in the reservoirs; and (v) control circuitry for selectively disintegrating the reservoir caps to release or expose the reservoir contents in vivo, wherein the reservoir caps comprises a first conductive metal layer coated with one or more protective layers comprising a noble metal film. For example, the first conductive metal layer can comprise titanium, and the noble metal film can comprise platinum. In preferred embodiments, the thickness of the protective metal layer is less than about 20% of the thickness of the first conductive metal layer.

In one embodiment, the control circuitry includes traces in electrical connection to the reservoir caps, wherein the traces comprise two or more layers of conductive materials. In one specific embodiment, the traces comprise a titanium/gold/titanium structure. In another specific embodiment, the reservoir cap comprises a titanium/platinum/titanium/platinum/titanium structure. In a further embodiment, the device includes a passivating layer covering the device except for at least a portion of the reservoir caps. In one embodiment, the substrate comprises a silicon wafer bonded to a glass wafer.

BRIEF DESCRIPTION OF THE DRAWINGS

FIG. 7 illustrates the steps involved in one process for removing unwanted tags from deposited features masking with additional layers in a one-step deposition process.

DETAILED DESCRIPTION OF THE INVENTION

Improved methods have been developed for fabricating a multi-reservoir device, such as an implantable micro-reservoir drug delivery or sensing device. New and improved devices made by these methods are also provided.

Herein, where the composition of a multilayer film is given, the materials composing the layer are listed in order of deposition, so that, for example, a Ti/Pt/Au multilayer film is fabricated on a substrate by depositing titanium, then platinum, then gold.

As used herein, the terms "comprise," "comprising," "include," and "including" are intended to be open, non-limiting terms, unless the contrary is expressly indicated.

The Fabrication Methods and Structures

Reservoir Fabrication

Figure 1A:
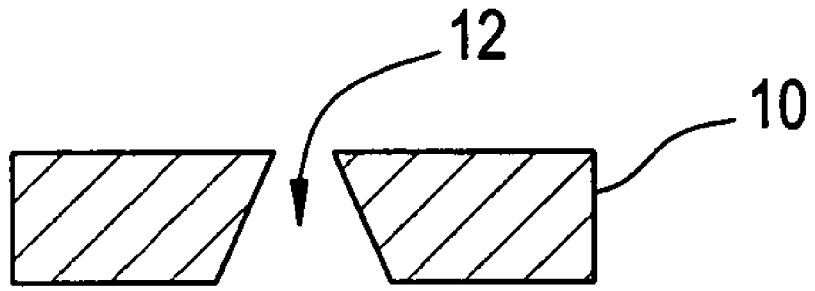
FIGS. 1A-B are cross-sectional views of a substrate with a reservoir therein, illustrating the area density limitations of pyramidal reservoirs in a single layer substrate (FIG. 1A) and a modification of this substrate with increased reservoir volume by using a multilayer substrate without increasing the exterior surface area occupied by the reservoirs (FIG. 1B).
Figure 1B:
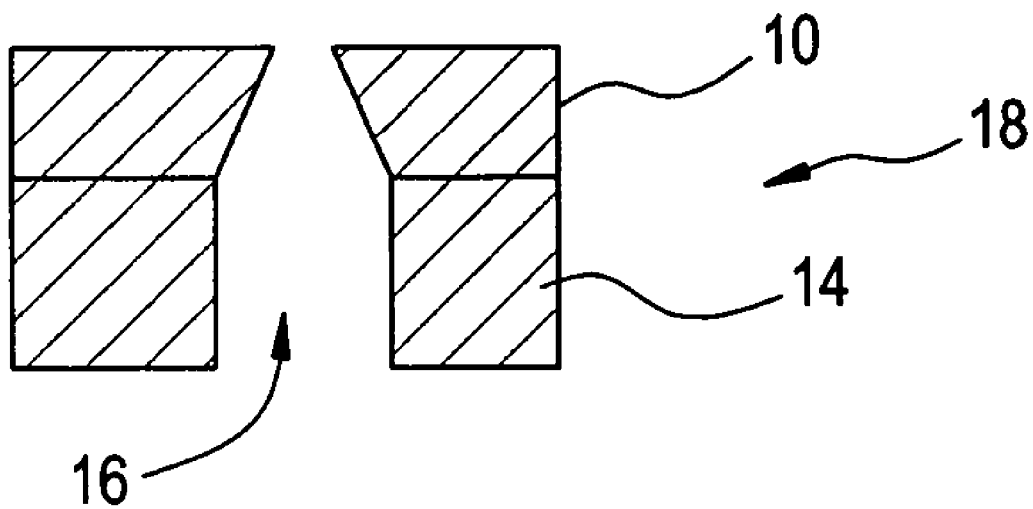

One method of increasing reservoir volume (and thus device reservoir density) is to attach/bond two or more substrate portions together. FIGS. 1A-B illustrates this concept, where first substrate portion 10 having a first reservoir 12 (FIG. 1A) is bonded to an additional substrate portion 14 with a through-substrate hole 16 aligned with the first reservoir to form a larger substrate 18 and reservoir (FIG. 1B). For simplicity, a single reservoir is illustrated, but the substrate typically and preferably includes a plurality of discrete, closely spaced reservoirs (e.g., in an array).

In one embodiment, the additional substrate portion is a glass wafer. Through-wafer holes in glass can be formed by wet chemical etching, electrochemical discharge drilling, ultrasonic drilling, laser drilling, electro discharge machining (EDM), or powder blasting, as known in the art. The glass wafer can be attached to the silicon wafer by the method of anodic bonding or the method of eutectic bonding, as described in U.S. patent application Publication No. 2003/0010808.

In another embodiment, the additional substrate portion is a silicon wafer. There are several ways to create suitable through-wafer holes in silicon. In one technique, an etch mask is deposited and patterned on one side of the wafer to create openings of the desired size. Deep reactive ion etching (DRIE) is then used to etch entirely through the wafer. In a variation of this embodiment, an etch mask is deposited and patterned on both sides of the wafer. DRIE is then used to etch partially through the wafer. The wafer is then turned over and DRIE is used to complete the etching process. This variation may be preferred if the etch depth is limited, for example, by mass transport limitations. By using this variation, the required etch depth could be reduced a factor of two by etching from both sides of the wafer. Suitable etch masks include photoresist, a metal such as nickel or chromium, or a dielectric such as thermally grown silicon dioxide. The etch mask can be removed if necessary after etching is completed.

Figure 2:
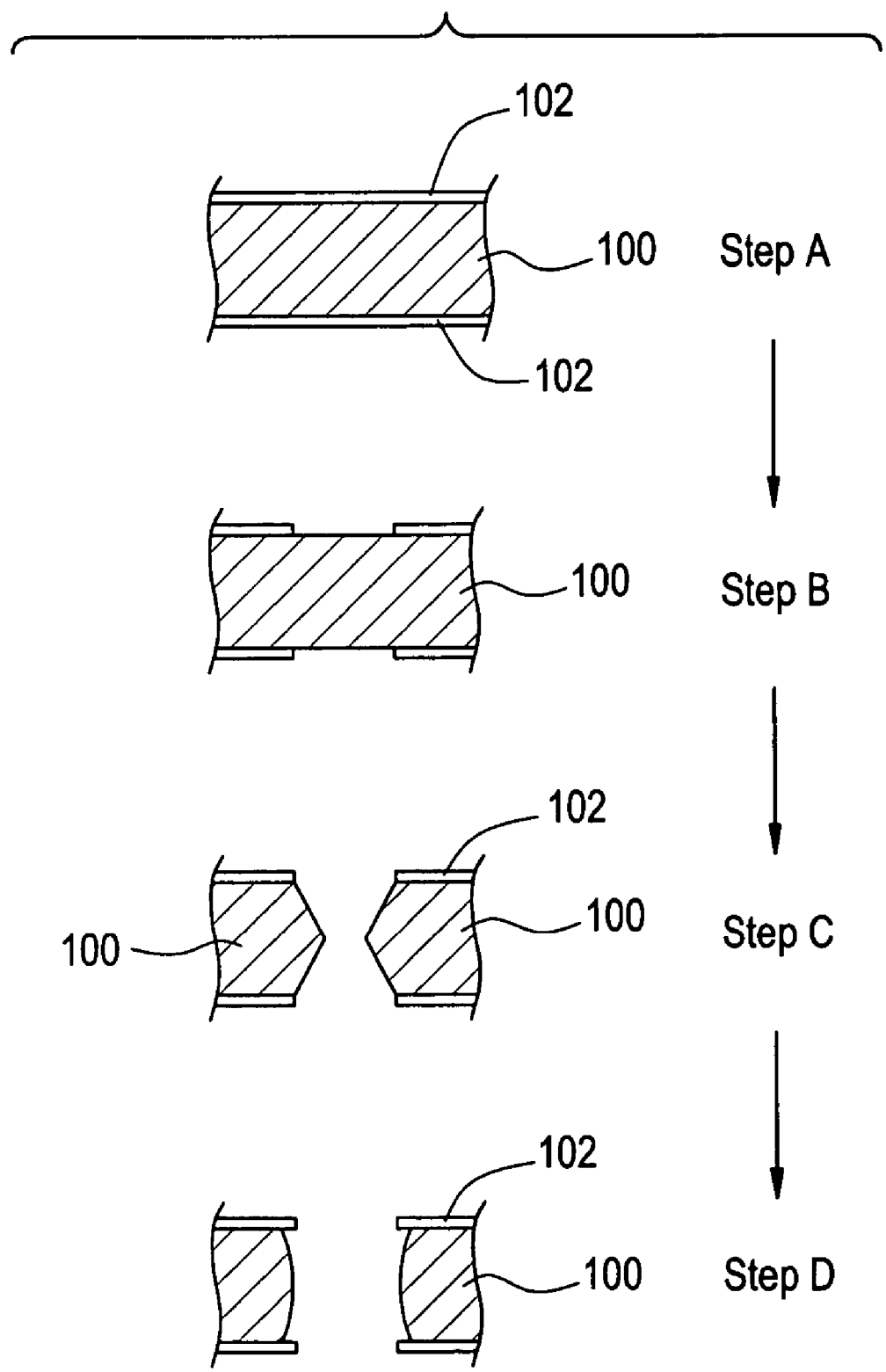
FIG. 2 illustrates the steps involved in one method of creating through-holes in a silicon substrate by an anisotropic etch and then smoothing the sidewalls of the hole (reservoir) by an isotropic etch.

Other variations of the method for creating through-holes is illustrated in FIG. 2. A single crystal silicon wafer 100 with a surface orientation in the direction of the (100) or (110) crystalline plane is used as the additional substrate portion. First, an etch mask 102 is deposited (Step A) and patterned (Step B) on both sides of the wafer. Suitable etch masks include silicon nitride or silicon dioxide. Then, an anisotropic silicon etchant, such as KOH or TMAH, is used to etch cavities in both sides until the cavities meet (Step C). In an optional variation, an isotropic silicon etchant is used after the through-wafer hole is created to widen the hole, or smooth the surfaces of the hole, or both (Step D). For example, the anisotropic silicon etchant KOH can leave sharp concave edges because etching occurs along crystallographic planes. These corners undesirably can serve as stress concentrators, lowering the strength of the substrate. By using an isotropic etchant to round these corners, the strength of the substrate can be increased. Suitable isotropic silicon etchants include aqueous, gaseous, and plasma-based chemistries. For example, an aqueous composition including HF and $HNO_3$ could be used, as described in Robbins & Schwarz, *J. Electrochem. Soc.* 106 (1959). Alternatively, gaseous $XeF_2$ or $BrF_3$ or a fluorine-containing plasma could be used.

The additional substrate portion, containing through-wafer holes, and the original substrate portion, which could include the reservoir cap and disintegration circuitry of the device, can be joined by several methods. In one embodiment, silicon direct bonding at a temperature of approximately 1000° C., as described in Tong & Gosele, "*Science and Technology of Semiconductor Wafer Bonding*" (John Wiley & Sons, USA) (1999), is used to join the two wafer, i.e., the two substrate portions. In another embodiment, an intermediate film is used to join the wafers. For example, a borosilicate glass could be deposited on one or both of the wafers by sputtering and the wafers joined by heating the stack beyond the softening point of the glass. Alternatively, the borosilicate glass contains an amount of sodium or lithium to provide mobile ions, and the wafers are joined in an electrostatic method (anodic bonding) as described in Hanneborg et al., *J. Micromech. Microeng.* 2(3) (1992). In yet another embodiment, the intermediate film consists of a metal (such as gold) and the wafers are joined by thermocompression bonding, as described in Tsau, et al., *J. Microelectromechanical Systems*, 11(6) (2002). Alternatively, a gold or gold-silicon film is used and the wafers are joined by the method of Au—Si eutectic bonding, as known in the art.

The substrate material can be formed from a variety of materials. While the methods are described herein often with reference to using a silicon substrate, non-silicon substrates are contemplated, which can broaden the range of useful fabrication methods available for making the devices described herein. Examples of suitable materials include ceramics, metals, and polymers, and examples of fabrication methods include Low Temperature Co-Fired Ceramic (LTCC) methods for ceramics (e.g., aligning/laminating green ceramics and then firing them) and thermo-compression molding for polymers.

In another aspect, it may be desirable to provide the interior sidewalls of the reservoirs with a protective surface, e.g., by coating the interior sidewalls or to otherwise provide a favorable surface chemistry. Single crystal silicon, for instance, is known to be etched under in vivo conditions. So, to protect this surface, it may be desirable to physically deposit or chemically grow on the sidewalls a protective material. In one embodiment, a metal such as gold or platinum is deposited on the sidewalls by physical vapor deposition. In another embodiment, a metal is deposited on the sidewalls and annealed to form a silicide. In yet another embodiment, silicon dioxide is thermally grown on the sidewalls to provide a hydrophilic surface that would promote wetting when the reservoir is filled with drug. In a further embodiment, the reservoir sidewalls are coated with titanium or silicon nitride. In still another embodiment, the silicon sidewalls are doped with an impurity to improve resistance to etching under in vivo conditions. For instance, boron at high levels of doping would be an example of a dopant that would decrease dissolution/etching when exposed to chemicals or to fluids in a human or other mammalian body. In a further embodiment, the sidewalls have one or more layers of material deposited on them. This can be highly useful or even necessary to protect the walls of the reservoir exposed to a range of chemicals, drugs, and/or in vivo fluids. Examples of coating materials include diamond-like carbon, silicon carbide, and other carbides.

Reservoir Cap Fabrication

In some embodiments, a reservoir cap material that is electrically favorable for device operation is incompatible with certain (additional or optional) fabrication steps. U.S. patent application Publication No. 2004/0121486 A1 to Uhland, et al. describes the use of reservoirs caps made of conductors such as titanium or silicon doped with an impurity. However, where fabrication includes depositing the reservoir cap material on a suspended dielectric membrane and then removing the membrane from underneath by plasma etching with a fluorine-containing gas such as $CF_4$ or $CHF_3$, as described in U.S. Pat. No. 5,797,898, then a reservoir cap made of titanium or silicon would be partially or completely etched during reactive ion etching to remove the dielectric membrane, as it is known in the art that titanium and silicon are chemically etched in plasmas containing fluorine. One method of preventing the reservoir cap from being etched is to add a protective layer of material that would not be chemically etched in fluorine-containing plasma. Examples of suitable layers include noble metals such as gold, platinum, or iridium, or alloys thereof. The layer is desirably thick enough to form a contiguous layer, but not so thick that the electrical resistance of the reservoir cap is significantly affected. For example, a suitable thickness and composition for a protective layer would be 40 nm of platinum for a reservoir cap with an initial thickness and composition of 300 nm titanium. In addition, an adhesion layer such as titanium or chromium preferably may be included between the dielectric material and the protective layer. One example of a suitable thickness and composition for this adhesion layer would be 10 nm of titanium. Other thicknesses of the reservoir cap layer and the protective layers are contemplated.

Similarly, it may be desirable to partially or completely passivate or protect the reservoir cap before implantation by depositing a dielectric such as silicon dioxide on its surface, as described in U.S. Pat. No. 5,797,898. Silicon dioxide is typically patterned by using hydrofluoric acid, which also attacks titanium. A reservoir cap made of titanium would be partially or completely etched through during hydrofluoric acid etching while the passivation layer is being patterned. As described above, a protective layer can be added to the reservoir cap. Examples of suitable layers include noble metals such as gold, platinum, or iridium, or alloys thereof. Again, an adhesion layer such as titanium preferably can be added between the passivating dielectric material and the protective layer.

Figure 3A:
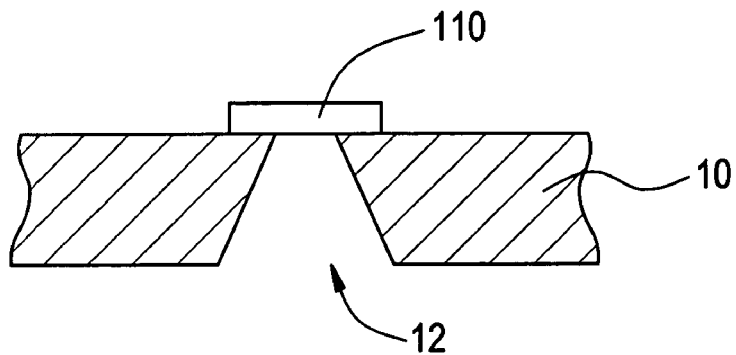
FIGS. 3A-B are cross-sectional views of a substrate and single reservoir covered by a single-layer reservoir cap (FIG. 3A) or by a multi-layer reservoir cap with protective layers (FIG. 3B).
Figure 3B:
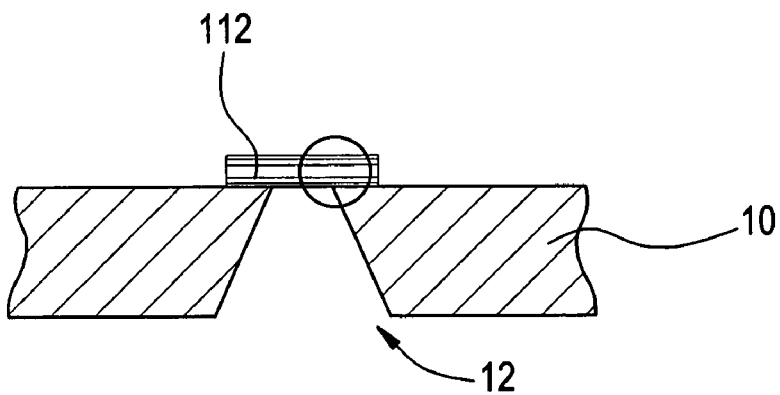
Figure 3C:
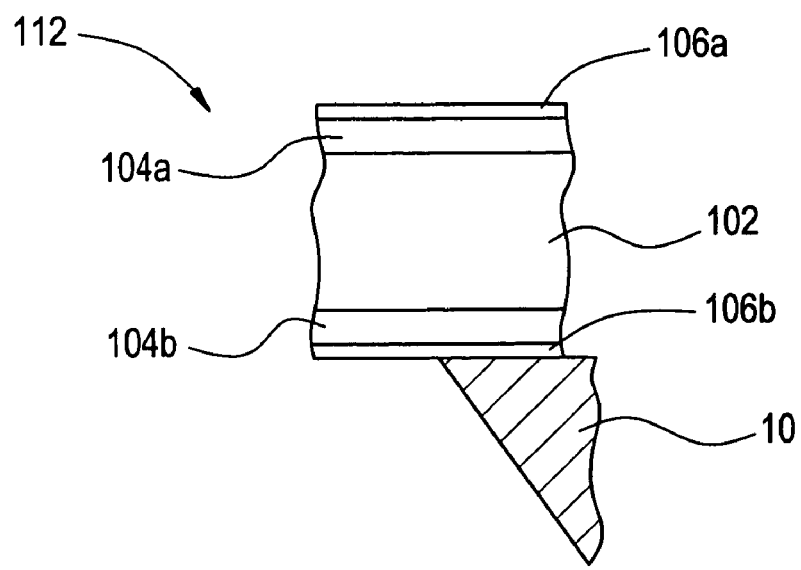
FIG. 3C details the structure of the multi-layer reservoir cap in FIG. 3B.

FIG. 3A illustrates substrate 10, reservoir 12, and unprotected reservoir cap 110, which is made of titanium. FIG. 3B illustrates substrate 10, reservoir 12, and protected reservoir cap 112. As detailed in FIG. 3C, the protected reservoir cap 112 includes reservoir cap 102 between layers of protective platinum 104a, 104b and titanium adhesion layers 106a, 106b. If a protective layer of noble metal, such as platinum, is added to both sides of the original reservoir cap, then a reservoir cap comprising a reactive material, such as titanium, is protected from oxidation or reaction with the environment. The protective layers on both sides can have equal thickness, but other ratios of thickness may also be appropriate. Similarly, the adhesion layers on both sides can have equal thickness, but other ratios of thickness may also be appropriate. These protective layers on the reservoir cap may, in some embodiments, also provide a level of mechanical support to the reservoir cap structure. In a preferred embodiment, the protective layer(s) are made of a conductive noble metal film and the primary reservoir cap layer is a conductive non-noble metal layer. Typically the thickness of each protective layer is less than about 20% of the thickness of the reservoir cap layer. In one embodiment, protected reservoir cap 112 comprises 12.5 nm Ti/40 nm Pt/300 nm Ti/40 nm Pt/12.5 nm Ti.

In one embodiment, the stack of layers forming protected reservoir cap 112 is deposited in one process step by a physical vapor deposition method, such as evaporation or sputtering. If a noble metal such as platinum is deposited as part of the reservoir cap, methods of patterning the reservoir cap by wet chemical etching may be limited, as platinum is resistant to many chemical etchants. Moreover, a multilayer or alloy film can be difficult to pattern by wet chemical etching when the layers of the film cannot all be etched by the same etchant. For example, consider a reservoir cap partially or completely comprising a gold-silicon alloy. An aqueous solution of $KI+I_2$ is commonly used to etch gold, and aqueous potassium hydroxide is commonly used to etch silicon, but these are not be suitable etchants for certain other materials. It is common to pattern multilayer or alloy films with the liftoff process.

In the liftoff process, one or more layers of photoresist are deposited and patterned before film deposition, and windows are opened where the film is desired on the substrate. After film deposition, the photoresist is removed in a solvent, leaving the film remaining where it is desired on the finished device. The advantage of the liftoff process is that a multilayer or alloy film can be patterned without chemically etching each component of the film.

Variation on the liftoff process are known in the art. For example, U.S. Pat. No. 4,024,293 to Hatzakis discloses a method of using a bilayer stack of two photoresists, developed in two different developers that are mutually exclusive. In addition, U.S. Pat. No. 3,934,057 to Moreau discloses a method of using a stack of two or more layers of photoresist that have successively decreasing solubility in a single developer. This process also leaves an overhang that is favorable for performing the liftoff process. Bilayer lift-off resists are commercially available. See e.g., http://www.microchem.com/products/lor.htm. There are also single-layer photoresists that form an overhanging slope favorable to lift off. The extent of the overhang is determined by the exposure time and developing time.

Figure 4:
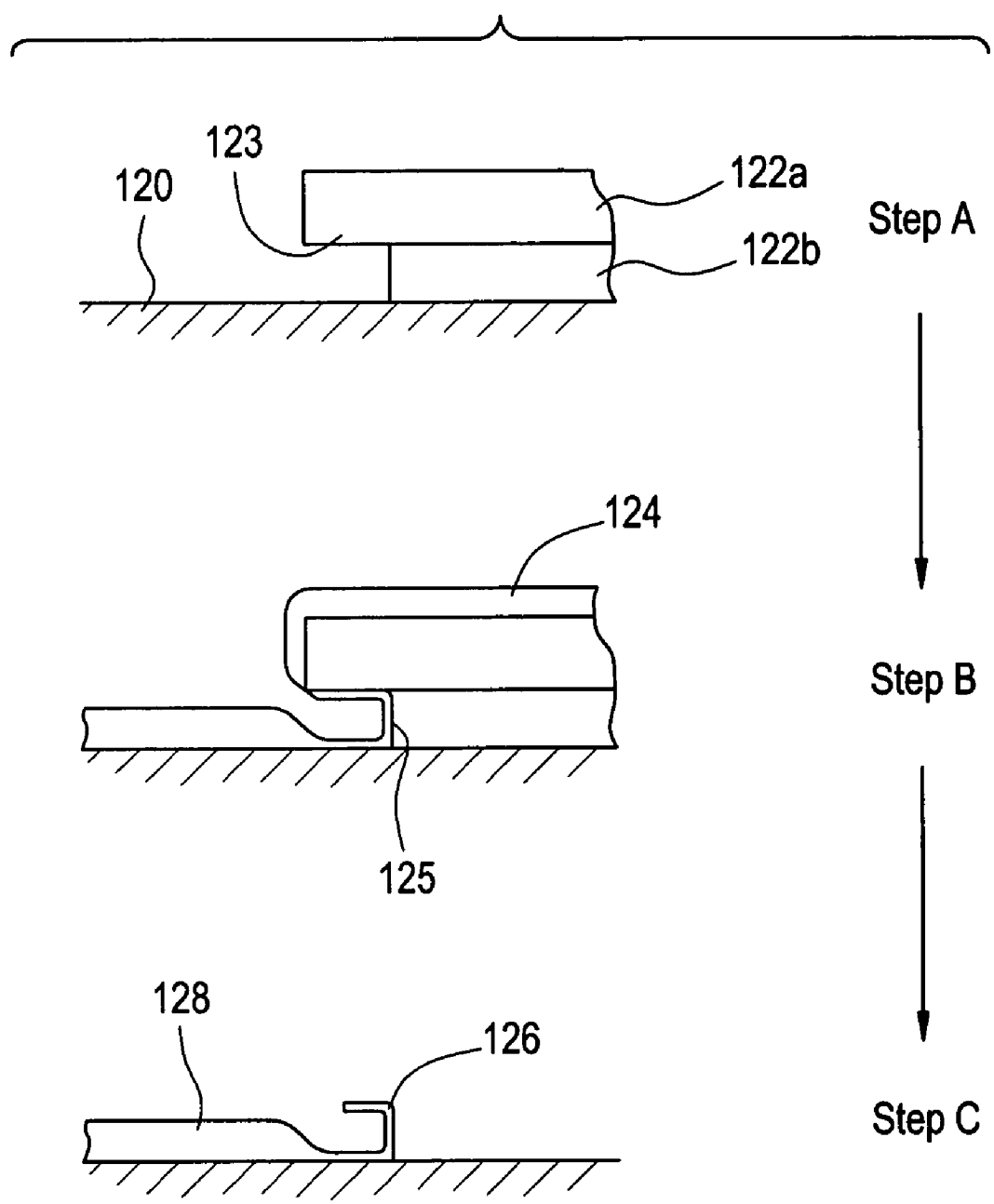
FIG. 4 illustrates the steps involved in one process method, showing remaining material left after combining the liftoff process with sputter deposition.

These photoresist methods can be used to pattern a reservoir cap such as those containing a gold-silicon alloy, or a multilayer film comprising platinum and titanium. The liftoff process is well suited to film deposition by evaporation; however, problems can arise when using the liftoff process with sputtering. Sputter deposition is preferred for some applications because of its capability for high processing throughput and conformal substrate coating. However, some material tends to deposit on the sidewalls of the photoresist because sputter deposition is not a line-of-sight deposition process. When the liftoff process is completed by removing the photoresist, the material sputtered under the photoresist overhang can remain, and this remaining material can interfere in the subsequent deposition of another film. FIG. 4 illustrates this process: bilayer stack of two photoresists 122a, 122b is deposited onto substrate 120, creating overhang 123 (Step A); reservoir cap material 124 is sputtered onto the substrate and photoresist, including onto the photoresist sidewall 125 (Step B); and photoresist is removed, leaving reservoir cap 128 and extra material 126, called a tag or wing (Step C).

Figure 5A:
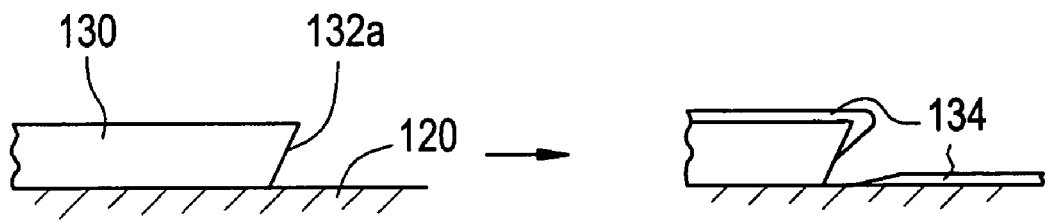
FIGS. 5A-C are cross-sectional views of feature sidewalls with three different angles, which show unfavorable and favorable sidewall angles and typical results after film deposition.
Figure 5B:
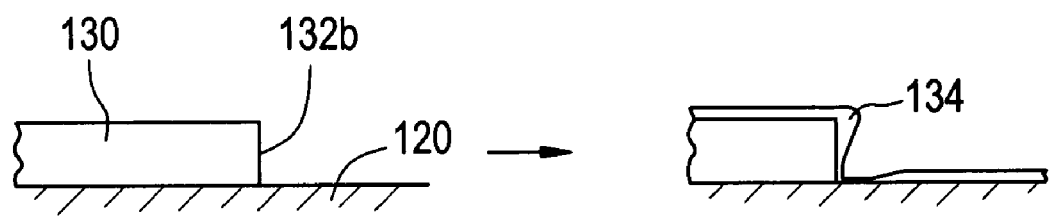
Figure 5C:
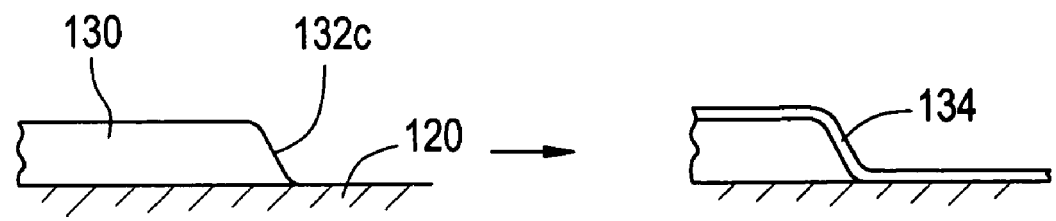

When combining sputter deposition with a liftoff process, it is desirable to produce features with smooth sidewalls. It is noted that in this paragraph, the term "sidewalls" does not refer to the inner surface of the reservoirs in the substrate, but rather refers to metal deposition and patterning processes of features, typically on top of the substrate, the surfaces of the feature (e.g., reservoir cap) that are other than parallel to the substrate surface. That is, it may be desirable to have features with smooth contours, transitions, or edges, rather than abrupt changes in surface topography or sharp edges of features, so that these features are then easily covered with another film, such as a dielectric or additional conductive layer. Illustrations of "favorable" and "unfavorable" sidewalls are shown in FIGS. 5A-C. In these figures, substrate 120 has feature 130, with different sidewalls 132a, 132b, and 132c, covered by material layer 134 using physical vapor deposition (PVD) or chemical vapor deposition (CVD). The "favorable/unfavorable" classification is based on the desirability of depositing multiple layers of material on top of each other while achieving good contact/continuity between the layers. The exact slope angle required to make a favorable connection depends on the material being deposited over the slope and the method of deposition. Based on these objectives, FIGS. 5A and 5B would generally be considered to illustrate unfavorable sidewalls, and FIG. 5C would generally be considered to illustrate favorable sidewalls. There are, however, device designs and fabrication methods where the embodiments of FIGS. 5A or 5B would be considered favorable, for example, where continuity in the deposited film is unnecessary or undesirable.

Figure 6A:
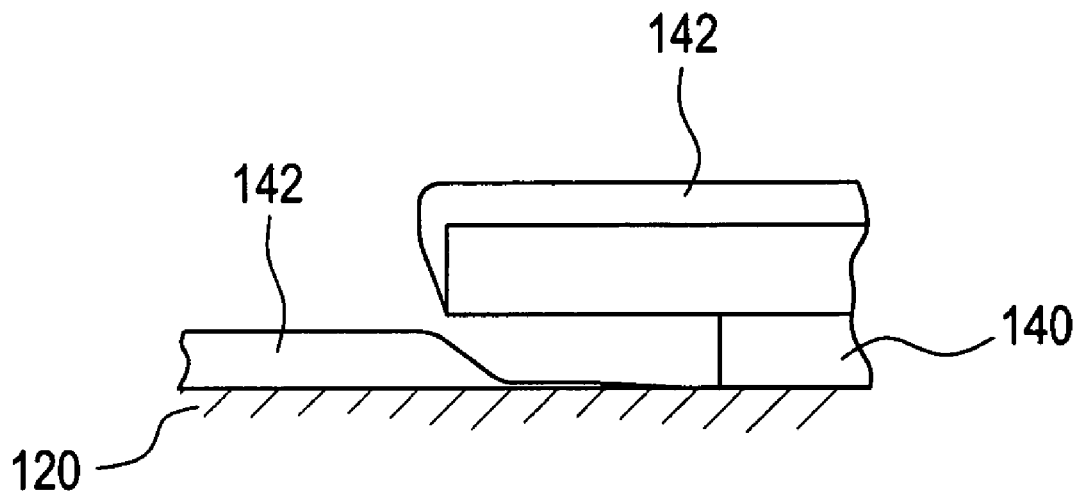
FIGS. 6A-B are cross-sectional views showing the sidewalls resulting from using an increased photoresist overhang (FIG. 6A) or by reducing the pressure during sputtering or using a collimator (FIG. 6B).
Figure 6B:
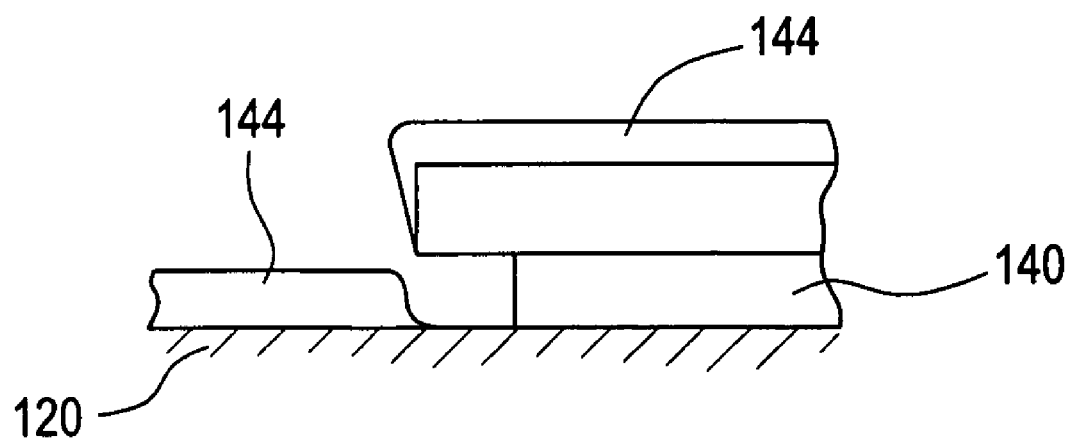

Favorable feature sidewalls can be achieved by using any of several techniques. In one embodiment of the bilayer liftoff process, shown in FIG. 6A, the bottom photoresist 140 is laterally etched to a sufficient distance that a negligible amount of material 142 is deposited on the sidewall of the bottom photoresist. In another embodiment, shown in FIG. 6B, the conformal nature of sputter deposition is adjusted by decreasing the pressure in the vacuum chamber during deposition or by incorporating a collimator, as described in U.S. Pat. No. 4,824,544 to Mikalesen, et al., resulting in layer 144 having a more steeply angled sidewall and a negligible amount of material 144 deposited on the sidewall of the bottom photoresist 140.

Figure 12A:
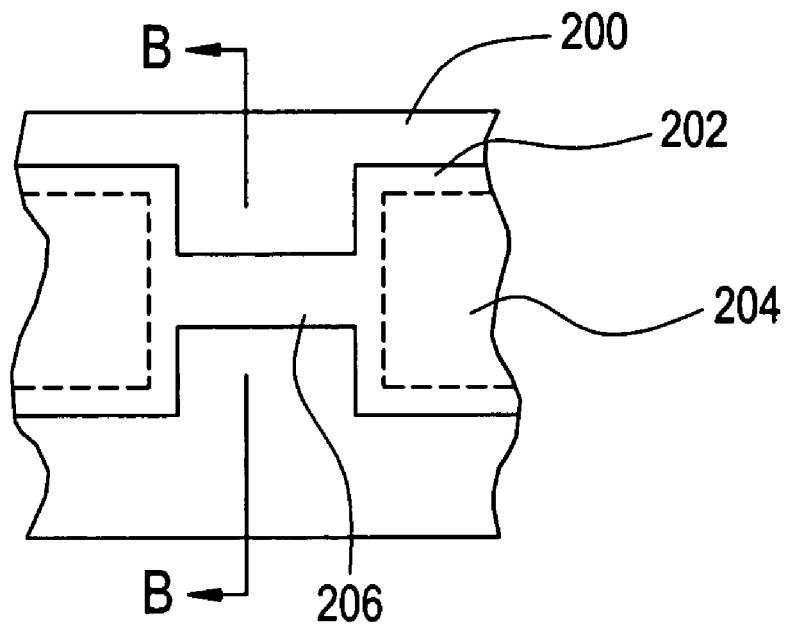
FIGS. 12A-B show a plan view (FIG. 12A) and a cross-sectional view (FIG. 12B) of an intermediate structure in which a bilayer photoresist is used to create bridges over the substrate which can be used in a subsequent metal deposition process to vary the thickness of the deposited metal layer.
Figure 12B:
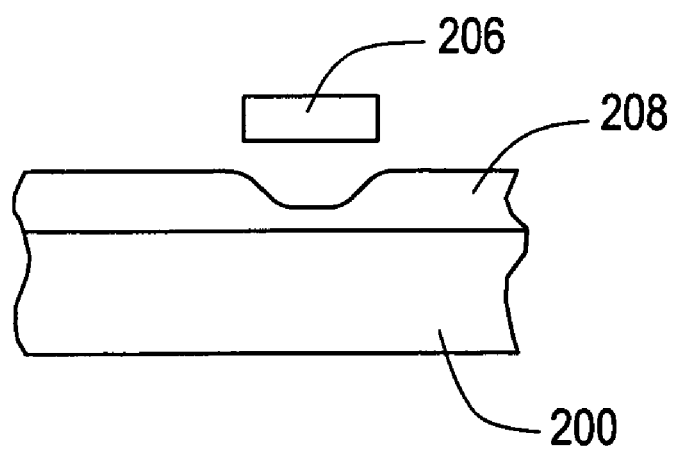

In a further embodiment, a microfabrication process has been developed applicable to making metal films for a variety of purposes, not limited to medical devices or to micro-reservoir devices, but would be broadly applicable to any microfabricated device that includes metal layers (e.g., integrated circuits for computers and other electronic devices). Advantageously, the process provides a way to produce a metal film or patterned metal feature with a thickness variation within a single metal layer, without subsequently etching the metal layer. In a preferred embodiment, the method is used to form reservoir caps, traces, for both. The process provides continuous metal films deposited with varying thicknesses, with a smooth transition from one thickness to another. Advantageously, it can be performed in one metal deposition step. In one embodiment, a bilayer of photoresist is applied to a substrate and the lower (liftoff) resist is then completely etched away in select areas to form one or more "bridges" composed of the upper (imaging) resist. These one or more bridges then can be used to make a continuous metal film of varying thickness and a smooth contour. This concept is illustrated in FIGS. 12A-B, where substrate 200 has bilayer photoresist comprising imaging resist 202 and liftoff resist 204, which is etched to form bridge 206. Metal layer 208 can then be deposited, where bridge 206 has influenced the thickness of the metal layer therebelow. The thickness and variation of the thickness can be controlled by the choice of the metal deposition method (e.g., e-beam, sputtering, ion beam), the conditions that affect directionality (e.g., process pressure and temperature), the width of the bridge, and the rate of metal deposition. Multiple bridges and varying shapes of bridges can readily be created (e.g., by patterning of the photoresist) to further control thickness variations across the metal surface area.

Fabrication of Traces

The term "traces," as used herein, is used to describe the on-chip (i.e., on substrate) wiring or conductive features that electrically connect the reservoir cap to other features elsewhere on the chip.

To form an operable electric circuit through the reservoir caps as described in U.S. patent application Publication No. 2004/0121486 A1 to Uhland, et al., the reservoir caps are connected to a power source and to control electronics, on or off the device. It is desirable to keep the power requirements low for an implantable device. If a certain electrical current is required to rupture the reservoir cap, then the total voltage required for activation is proportional to this current and the total resistance in the circuit. It is therefore desirable to reduce the resistance of the circuitry in series with the reservoir cap.

Traces with a favorably low resistance can be constructed by depositing materials with a low electrical resistivity and by using features that are as wide or as thick as possible. For example, low-resistivity materials such as gold, silver, copper, or aluminum are appropriate materials, while gold is preferred for an implantable device due to its biocompatibility and biostability. The maximum width of the traces is necessarily limited by the space available on the substrate surface of the microchip. The maximum thickness may be limited by the deposition and patterning processes used to fabricate the traces.

In some cases, substrate surface area limitations (e.g., where the substrate surface area is small and contains an array of many closely packed reservoirs) may impact the number and placement of the traces. In such instances, the traces can be overlaid if an appropriate insulator or dielectric material is deposited between the overlaid traces. In such cases, the traces typically would be connected electrically through vias for operation.

When it is necessary to fabricate a conducting feature in electrical contact with another conducting feature of the micro-reservoir device, techniques known in the art can be used or adapted to promote good physical and electrical contact. For example, a separate adhesion layer can be included to promote adhesion of the electrical trace to a dielectric layer, but may not be needed or desirable in all embodiments. Adhesion can be promoted by using adhesion layers on the contacting surfaces. For example, a layer comprising 12.5 nm Ti/2000 nm Au/12.5 nm Ti may be deposited and patterned as a trace feature. Following this step, an additional layer comprising 12.5 nm Ti/2000 nm Au can be deposited over the first metal layer, where the titanium is used as an adhesion layer. Other layer thicknesses are contemplated. Another way of promoting a good physical and electrical contact is to perform an in situ sputter clean immediately before the second metal layer is deposited by sputter deposition. It is necessary to maintain a vacuum in the deposition chamber between the cleaning and deposition steps to avoid contamination. In this approach, intermediate adhesion layers are not always necessary, and so, for example, a layer comprising 2000 nm Au can be deposited over a layer comprising 12.5 nm Ti/2000 nm Au. If a gold trace surface is absolutely (atomically) clean (e.g., with in situ sputtering), a Ti or other adhesion layer may not be needed.

In one embodiment, the trace features can be patterned by combining sputter deposition with a liftoff process. As described above, this combination may produce "tags" or "wings" of material at the edge of features. As illustrated in FIG. 7, a useful way to remove these tags 152 is to deposit a mask layer 154 over the trace material 150 (Step A). This mask layer 154 is desirably thinner than the trace material 150. Suitable ratios of thickness range from about 1:5 to about 1:1000. After deposition and liftoff, both layers are exposed to an etchant that etches the trace material. Because the mask layer is of sufficient thickness over most of the feature to protect the trace material, the majority of the trace material is not etched. However, in the areas at the edge of the feature, the thickness of both the mask layer and the trace material is reduced. The trace material is therefore vulnerable to etching in these areas, and the tags remaining after liftoff 152 will be removed, leaving sloped sidewalls 156 (Step B). In a typical embodiment, the thickness and materials are 2 μm Au for the trace material and 12.5 nm Ti for the mask layer. It is possible, but not necessary, for the mask layer to also serve as an adhesion layer to a dielectric layer that is deposited later.

Figure 10:
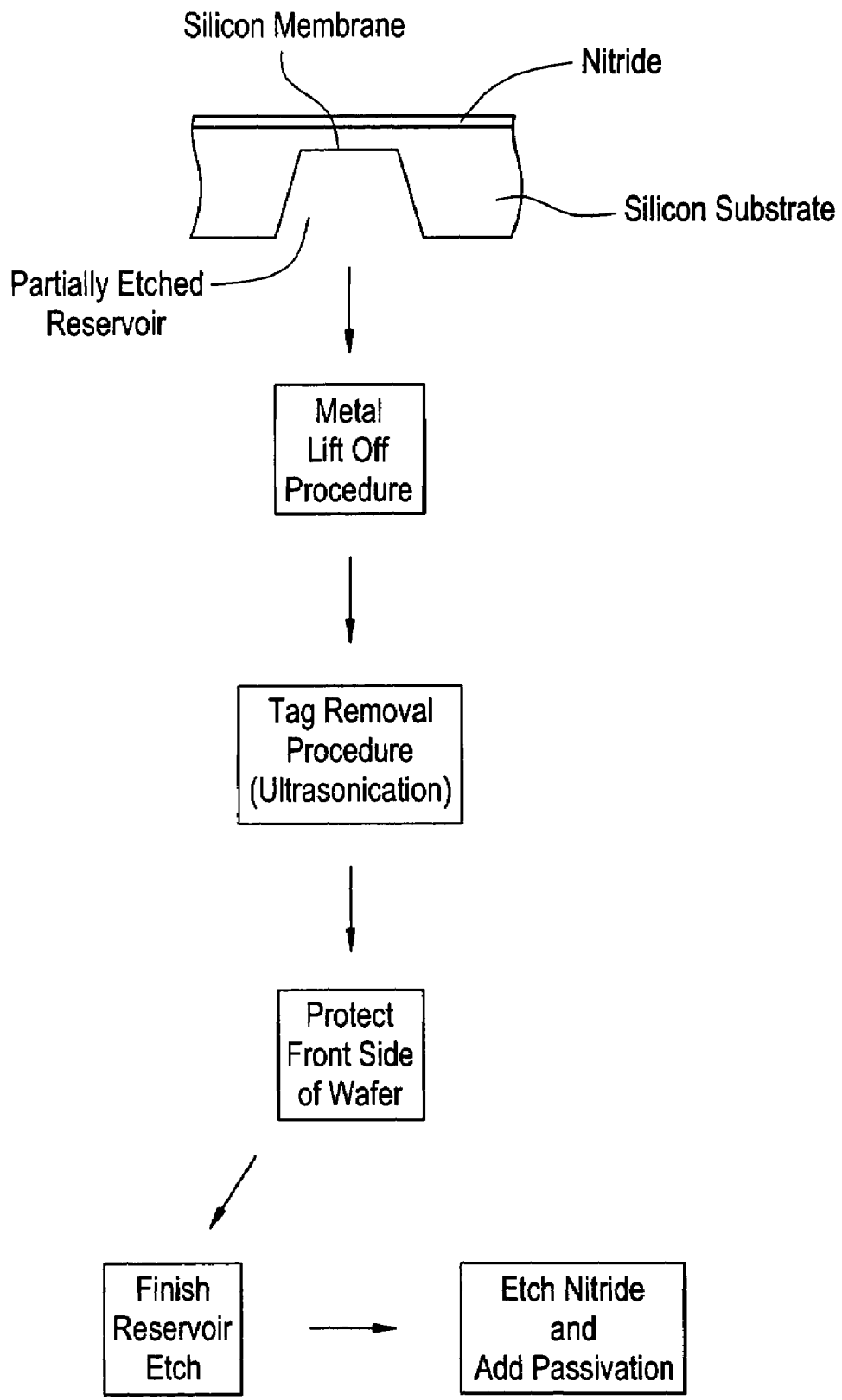
FIG. 10 is a process flow diagram and cross-sectional view of an intermediate structure in a fabrication process comprising a liftoff process, where unwanted tags are formed and removed before completion of the reservoir (forming) etching process. The figure shows the nitride layer reinforced by part of the silicon substrate that has not yet been etched away.
Figure 11:
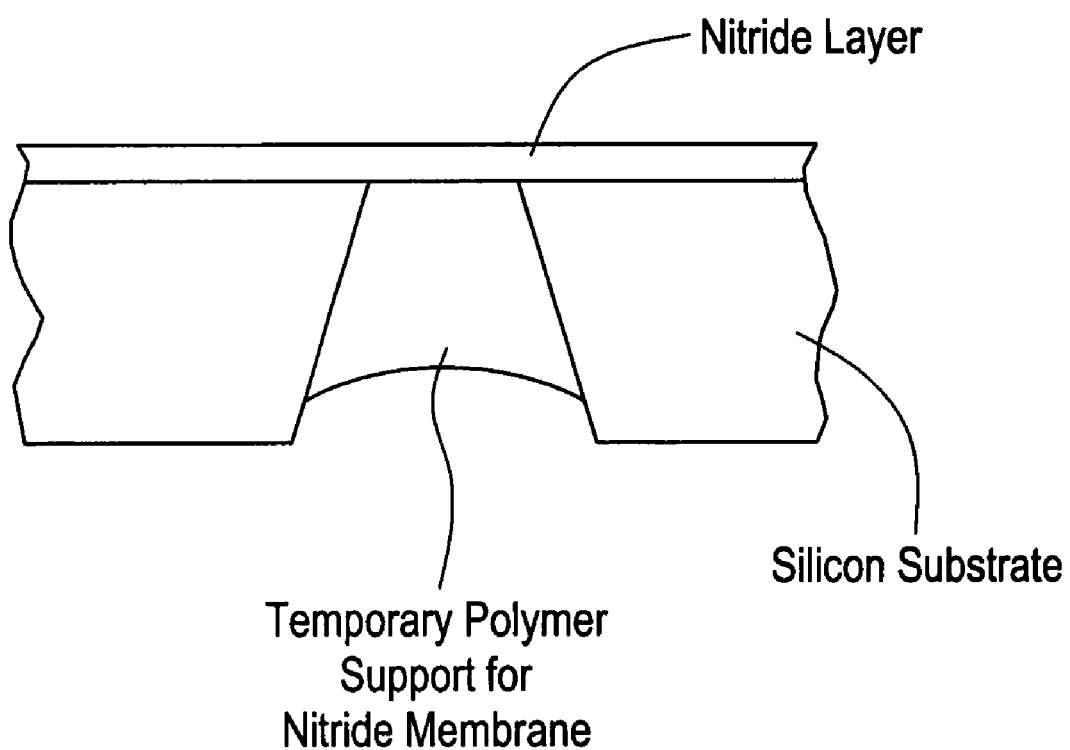
FIG. 11 is a cross-sectional view of another intermediate structure in a fabrication process comprising a liftoff process, where unwanted tags are formed and removed and a temporary, polymeric material fills the reservoir to support the nitride layer during tag removal.

In another approach, the liftoff tag is formed but removed in a step of the process. In one embodiment, ultrasonication is used after metal liftoff, but before nitride removal. For example, the ultrasonication step could be performed in water or in a dilute Au etch or a dilute Ti etch solution. If the nitride membrane alone is found to break due to the ultrasonication, then the reservoir could be partially etched with KOH to leave a thick $SiN_x$/Si membrane and sonicate after metal deposition and before completion of the KOH etch. See FIG. 10. Alternatively, the entire reservoir could be etched in KOH at the end of the process (i.e., after tag removal). In another embodiment, the device is sonicated to remove the tags when the reservoirs and nitride membrane are present, with the reservoir being filled (at least temporarily) with a material that can provide support to the membrane, as photoresist or another polymer. See FIG. 11.

Protective Features

U.S. Pat. No. 6,123,861 describes the use of a suspended dielectric membrane upon which a reservoir cap is fabricated, where the membrane is subsequently removed by etching. U.S. patent application Publication No. 2004/0121486 A1 to Uhland, et al. describes a method of operating reservoir caps by matrix addressing, where two conductive layers, comprising rows and columns, are separated by an intermediate dielectric layer. In some cases, however, the reservoir cap may not be compatible with the process used to deposit this dielectric layer. For example, for a reservoir cap partially or completely comprising a gold-silicon alloy at the eutectic composition, the melting point of the alloy is approximately 363° C. Therefore, this reservoir cap would be incompatible with a dielectric layer of silicon dioxide or silicon nitride deposited by the method of chemical vapor deposition around 350° C. or higher. It therefore would be desirable to fabricate a reservoir cap of such material after the dielectric layer has been deposited and patterned. In this case, the intermediate dielectric layer is deposited on the suspended dielectric membrane before being partially removed in preparation for the fabrication of the reservoir cap.

If the suspended membrane is attacked by the etching method used to pattern the intermediate dielectric layer, however, it can be difficult to stop the etch precisely on the suspended membrane, and the integrity of the membrane may be compromised by partial or complete etching. For example, the suspended dielectric membrane may be fabricated from silicon-rich silicon nitride deposited by LPCVD, as described in U.S. Pat. No. 5,797,898, and the intermediate dielectric layer may be fabricated from silicon dioxide, as described in U.S. patent application Publication No. 2004/0121486, that is deposited by PECVD and etched by reactive ion etching using $CF_4$. In this case, the method used to etch the dielectric layer will also attack the suspended membrane.

This problem can be avoided by fabricating a protective feature on the suspended membrane before the dielectric layer is deposited. This protective feature may comprise a layer or layers that can serve as an etch stop. For example, a layer comprising 5 nm Ti/300 nm Au/5 nm Ti can be deposited on the suspended membrane by the method of sputter deposition with liftoff, as described herein. In this multilayer film, the gold layer serves as an etch stop and the titanium serves as an adhesion layer. A dielectric layer can be deposited over this protective feature. When this dielectric layer is selectively or completely etched, for example by plasma etching with a fluorine-containing gas such as $CF_4$, the gold, which is not chemically etched by $CF_4$, serves as an etch stop. This modification protects the suspended dielectric membrane when a passivating dielectric layer is deposited and patterned over it. The protective feature can be partially or completely removed after the passivation layer is etched and before the reservoir cap is fabricated. The protective feature can also serve as an electrical connection between the traces and the reservoir cap.

Dielectric Layers

U.S. Pat. No. 5,797,898 describes the use of a dielectric film as a passivation layer to cover conductive layers on a drug delivery microchip. In addition, U.S. patent application Publication No. 2004/0121486 A1 to Uhland, et al. describes the use of a dielectric film to separate two conductive layers on a substrate of a micro-reservoir device. As with conductive films, it is desirable to fabricate these dielectric films with sloping sidewalls to promote good physical and electrical connections between conductive films.

One way to achieve sloping sidewalls in a dielectric film is to use an isotropic wet or dry chemical etch, which ideally produces sidewalls in the approximate shape of an arc. One example of this type of etching is the etching of silicon dioxide in hydrofluoric acid. Another way to achieve sloping sidewalls is to use an anisotropic etch, as is possible with reactive ion etching, and to use a organic etch mask that is etched in $O_2$. This type of organic etch masks includes standard positive-type and negative-type photoresists. By including $O_2$ in the reactive ion etching feed gases, the organic etch mask will be slightly eroded during etching. The resulting sidewall in the dielectric will have a slope that is favorable for later deposition of materials. An example of this type of etching is the reactive ion etching of a silicon dioxide film using 15 sccm $CF_4$, 2 sccm $O_2$, and 15 sccm He, at a pressure of 20 mtorr and a plasma power of 100 W. Variations of this process are contemplated.

Biostability

When a multi-reservoir medical device is to be implanted in the body, e.g., for drug delivery or biosensing, the device desirably is formed of or coated with a material that protects both the device in vivo and the patient. In one embodiment, a protective coating is deposited on the device. In one embodiment, the protective coating consists of silicon dioxide deposited by CVD. The silicon dioxide layer electrically insulates conductive layers (e.g., traces) from the body. In another embodiment, the protective coating includes an ion barrier, such as silicon nitride. Edell, *IEEE Trans. Biomedical Eng.*, BME-33(2) (1986) describes a layer of silicon dioxide deposited by CVD, followed by a layer of silicon nitride deposited by CVD. The silicon nitride serves as a barrier to sodium ions in the body, and the silicon dioxide layer insulates the silicon nitride layer from electrical potential on the device. The silicon dioxide improves the performance of the passivation layer because silicon nitride exposed to an electrical potential in an electrolyte is known to anodize and dissolve. In still another embodiment, the protective coating comprises a layer of silicon carbide deposited by CVD. Silicon carbide is harder than either silicon dioxide or silicon nitride and can therefore be used as a scratch-resistant coating. Silicon carbide is also more resistant to harsh chemical environments than either silicon dioxide or silicon nitride, as described in Flannery, *Sensor & Actuators*, A70 (1998). Other suitable coating materials include silicon oxycarbide (U.S. Pat. No. 5,755,759 to Cogan), titanium oxide, tantalum oxide (Christensen, et al, *J. Micromechanics Microengineering*, 9(2) (1999)), diamond-like carbon (U.S. Pat. No. 6,572,935 to He), and ultrananocrystalline diamond (U.S. patent application Publication No. 2003/0080085 to Greenberg).

In still further embodiments, the protective coating comprises or consists of a biocompatible metal layer. Representative examples include platinum, gold, iridium, titanium, or alloys thereof. In one embodiment, this metal is deposited on the part of the substrate that is exposed in vivo, as described in Hammerle, et al., *Biomaterials*, 23(3) (2002). If the metal has a sufficiently high resistivity and the layer is sufficiently thin, the amount of electrical current passing between reservoir caps during operation, or electrical cross-talk, is not significant. In another embodiment, the deposition of this metal layer also forms the reservoir caps. In yet another embodiment, openings are patterned in the metal layer around each reservoir to eliminate cross-talk. In yet another embodiment, a dielectric layer is first deposited on the microchip, followed by the metal, so that cross-talk is eliminated. As used herein "cross-talk" refers to and includes unwanted electrical interference, short-circuits, stray or induced currents, and the like.

Exemplary Embodiments

In one embodiment, the construction of a multi-reservoir (micro-reservoirs) device begins by fabricating an array of reservoirs in a silicon substrate leaving a suspended dielectric membrane. This is described, for example, in U.S. Pat. No. 5,797,898 and U.S. Pat. No. 6,123,861. Then other layers/features (e.g., conductive layers, dielectric layers) are constructed on the surface of the substrate, preferably using one or more of the techniques described above.

In one embodiment, traces with sloped sidewalls are fabricated by combining sputter deposition with a liftoff process. The reservoir caps are then fabricated by combining sputter cleaning and sputter deposition with a liftoff process. A passivating layer is deposited and patterned to open windows over the reservoir caps and over bond pads elsewhere on the substrate. In a preferred embodiment, the traces comprise 12.5 nm Ti/2000 nm Au/12.5 nm Ti, the reservoir cap comprises 12.5 nm Ti/40 nm Pt/300 nm Ti/40 nm Pt/12.5 nm Ti, and the passivating layer comprises 0.6 μm silicon oxide deposited by PECVD at 350° C. Anodic bonding is then used to attach a patterned Pyrex wafer, which serves as an additional substrate portion to increase reservoir volume.

Figure 8A:
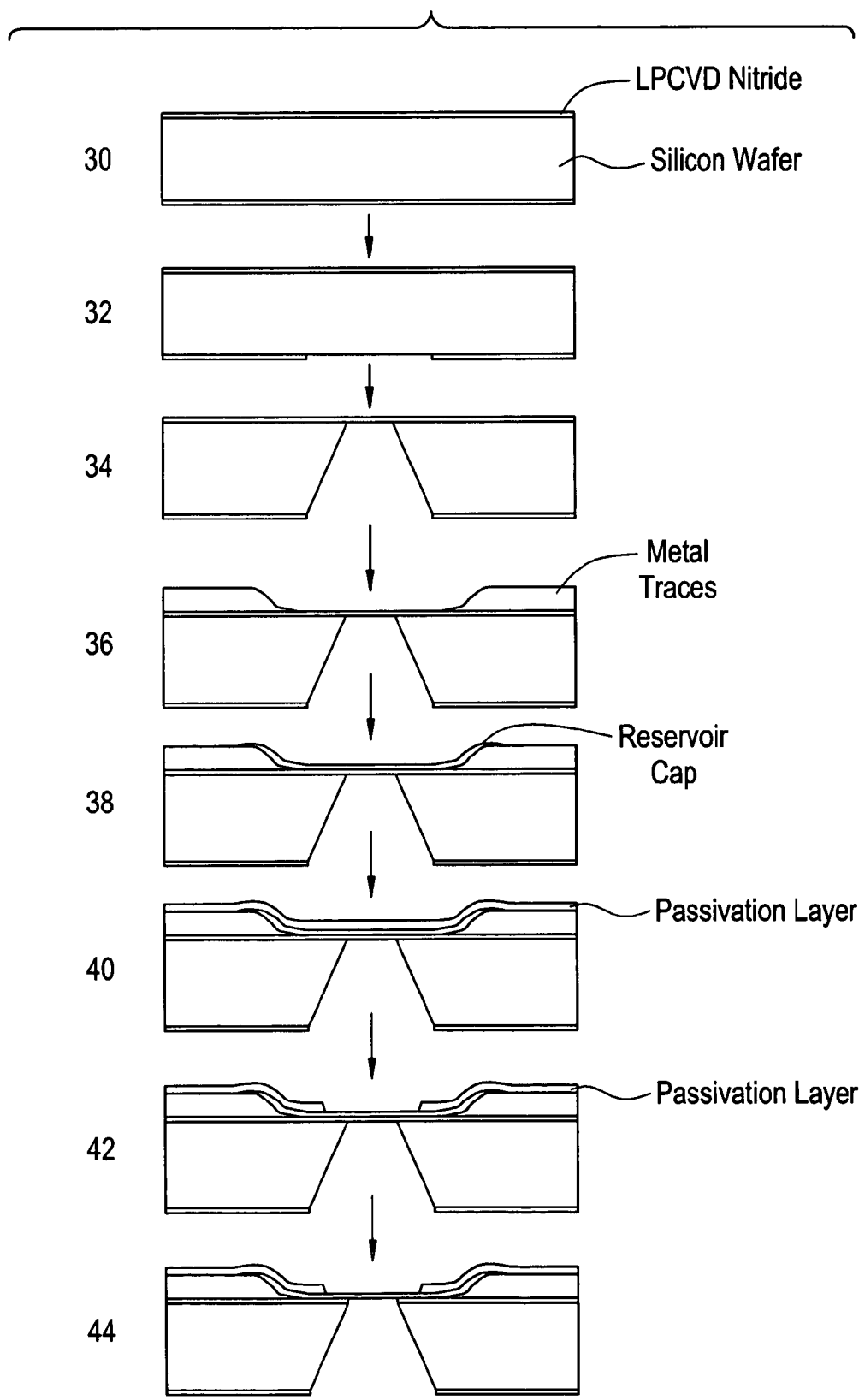
FIGS. 8A-B are cross-sectional views showing the fabrication steps (FIG. 8A) in one embodiment of the processes described herein, and a close-up of the resulting structure (FIG. 8B) made thereby.
Figure 8B:
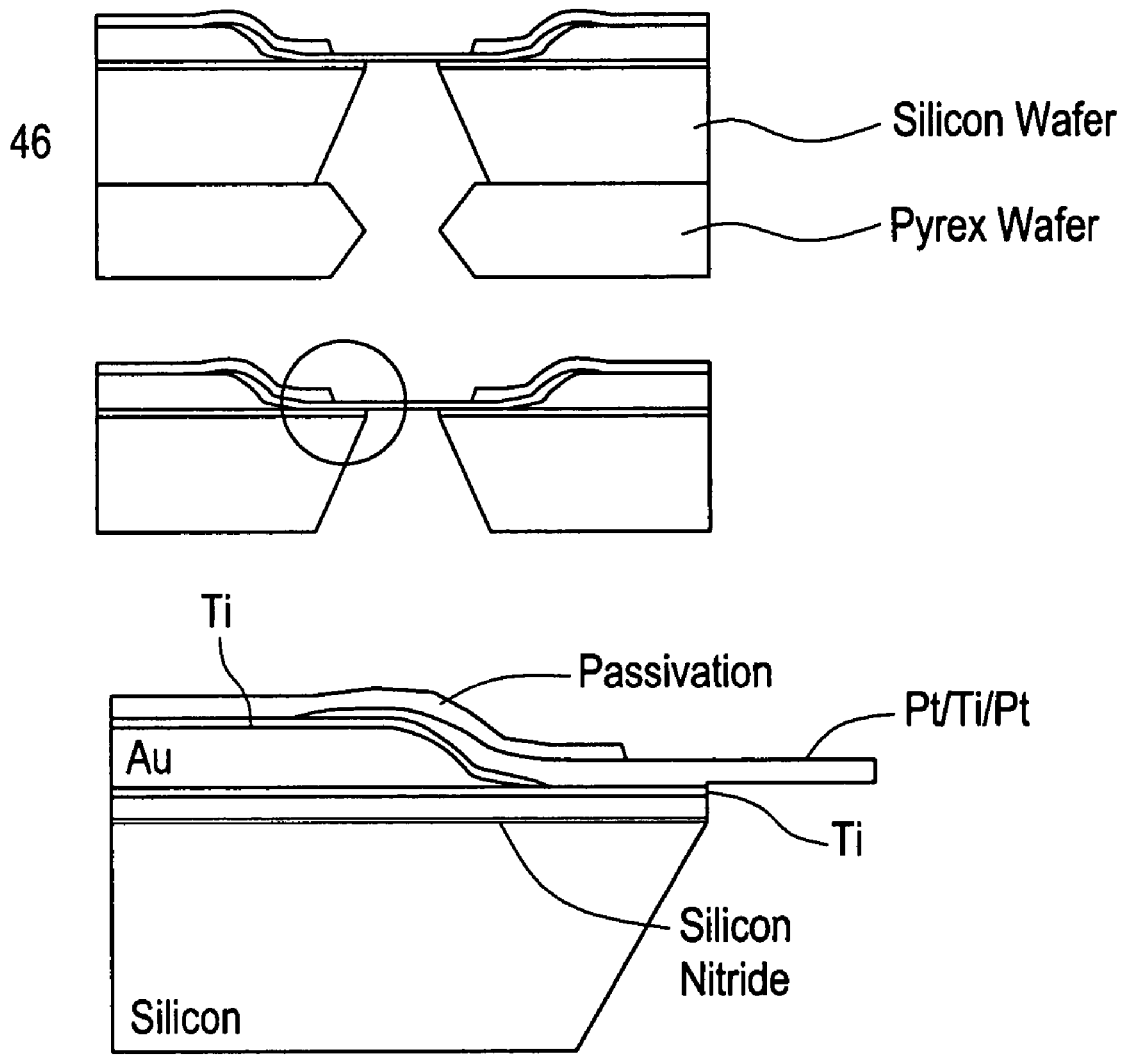

One specific example of this process is shown in FIG. 8A, with steps evenly numbered 30 through 46. The fabrication begins by depositing 200 nm low-stress nitride by Low Pressure Chemical Vapor Deposition (LPCVD) on a double side polished silicon wafer (30). The Nitride is patterned with photoresist and then etched using Reactive Ion Etching (RIE) techniques (32). The etching gases are $CE_4$ and $O_2$. After stripping the photoresist, the wafers are then anisotropically etched using 28% Potassium Hydroxide (KOH) solution. The patterned silicon nitride serves as an etch mask for the chemical etching of the exposed silicon (34). The metal traces are then deposited and patterned by liftoff (36). Alternatively, the metal traces can also be deposited and etched with a liquid etchant. After a quick $O_2$ plasma to clean the wafers, the reservoir cap is then deposited and patterned using lift off (38). The wafers are then passivated with 0.6 μm thick silicon dioxide layer (40). The passivation layer is deposited with Plasma Enhanced Chemical Vapor Deposition (PLCVD) using silane and nitrous oxide gases. The passivation layer is etched with RIE using $CHF_3$ and Ar gases (42). The backside nitride is etched from under the reservoir cap by RIE (44). The silicon wafer is then anodically bonded to a patterned Pyrex wafer (46). The anodic bonding temperature and voltage are 340° C. and 1000V, respectively. FIG. 8B illustrates the final device architecture, with the circled area in the upper structure shown enlarged to illustrate the structural details. Variations and modifications are this process are contemplated, including the use of different materials, different combinations of materials, different techniques for building and removing materials from select regions, and different proportions of the layers and shapes of the reservoir.

In another embodiment, the reservoir caps are fabricated by combining sputter deposition with a liftoff process. Traces are then fabricated by combining sputter cleaning and sputter deposition with a liftoff process. An intermediate dielectric layer is deposited and patterned to open windows over selective parts of the reservoirs caps and traces. In a variation, additional traces are fabricated in a second conductive layer by combining sputter cleaning and sputter deposition with a liftoff process. The sequence of depositing an intermediate dielectric layer and an additional conductive layer could be continued as desired to create additional traces.

In yet another embodiment, protective features are fabricated by deposition and patterning. Traces are then fabricated by combining sputter cleaning and sputter deposition with a liftoff process. A passivating layer is deposited and patterned to open windows over the protective features and over bond pads elsewhere on the substrate. The protective layer is removed from over the suspended membrane by wet chemical etching. The reservoir caps are fabricated by combining sputter cleaning and sputter deposition with a liftoff process. Anodic bonding is then used to attach a patterned glass (e.g., PYREX™) wafer, which serves as an additional substrate portion.

Figure 9A:
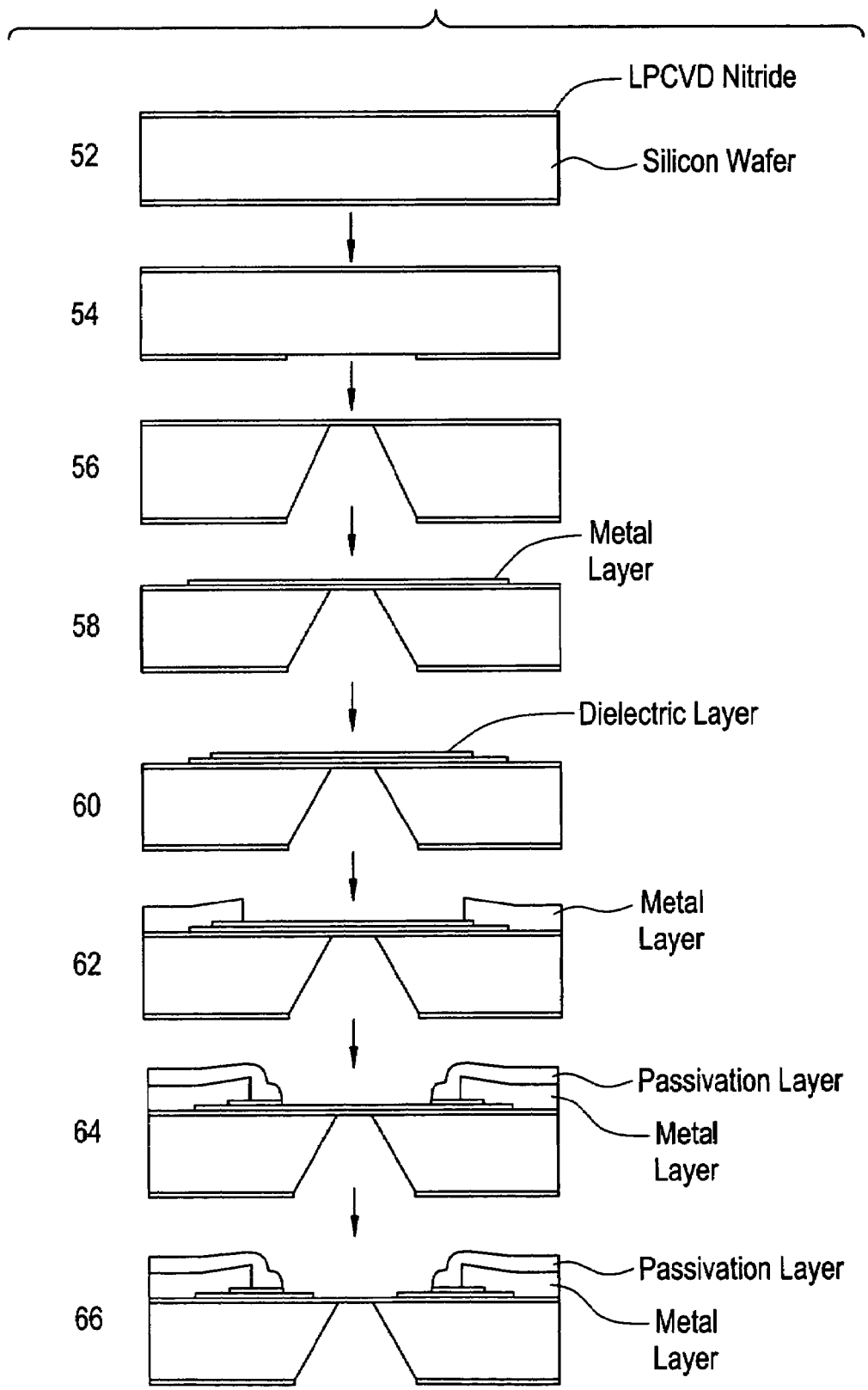
FIGS. 9A-B are cross-sectional views showing the fabrication steps in another embodiment of the processes described herein.
Figure 9B:
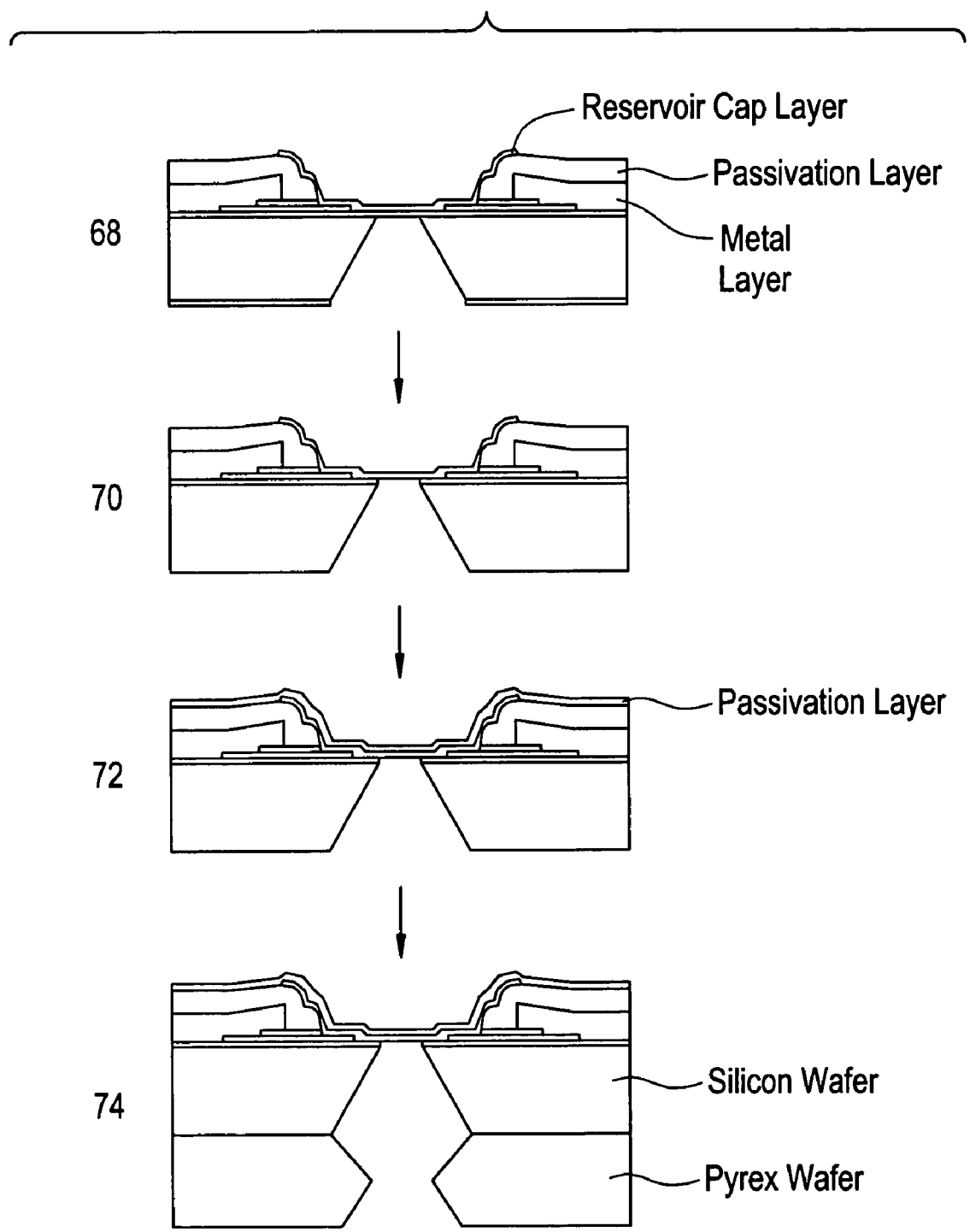

One specific example of this process is shown in FIGS. 9A-B, with steps evenly numbered 52 through 74. The fabrication begins by depositing 200 nm low stress nitride by LPCVD on a double side polished silicon wafer (52). The nitride is patterned with photoresist and then etched using RIE techniques (54). The etching RIE gases are $CF_4$ and $O_2$. After stripping the photoresist, the wafers are then anisotropically etched using a 28% potassium hydroxide (KOH) solution. The patterned silicon nitride serves as an etch mask for the chemical etching of the exposed silicon (56). Circular openings are used to reduce reservoir size variation caused by angular misalignment. The diameter is approximately 775 μm to allow for lateral (111) plane etching. The link metal layer is then deposited and patterned (58). The thickness/materials of the link layer is/are 12.5 nm Ti/0.3 μm Au/12.5 nm Ti. The link layer is used to electrically connect the traces to the reservoir cap. ID marks next to the bond pads are created in this step. The link layer is etched with a diluted HF/KI-based Au etch/diluted HF. A 300 nm dielectric layer is deposited by PECVD and etched with BHF (60). This dielectric layer is used as an etch "STOP". The trace metal layer is then deposited by sputtering. The thickness of the metal stack is 12.5 nm Ti/2.0 μm Au/12.5 nm Ti. The trace metal layer is etched by a series of sequential etches. For example, three etch steps could be used: dilute HF/KI-based Au etch/dilute HF (62). The link and ID marks are protected during etching by the STOP dielectric features. A passivation layer is then deposited by PECVD. The thickness/materials of the layer is/are 1.0 μm oxide/1.0 μm nitride/1.0 μm oxide. The passivation layer is then etched using RIE and BHF (64). This etching step can be finished using BHF to avoid etching LPCVD nitride if possible. The suspended nitride is protected during etching by the link metal feature. The ID marks next to the wells are created in this step. The link metal layer is then etched by dilute HF/KI based Au etch/dilute HF (66). The link feature is removed directly over the reservoir cap, but tabs remain to electrically connect the reservoir cap at the end of the process. The reservoir cap is then deposited using lift off (68). A sputter clean step is done prior to the reservoir cap deposition to provide a good metal contact. The silicon nitride and titanium is then removed under the reservoir cap using RIE (70). A conformal coating layer is deposited to passivate the chip (72). Finally, the silicon wafer is anodically bonded to a patterned Pyrex wafer (74). The anodic bonding temperature and voltage is 340° C. and 1000V, respectively. ps Additional Device and Component Details The Substrate and Reservoirs The substrate is the structural body (e.g., part of a device) in which, or on which, the reservoirs are formed. A reservoir can be a well, a container, or other space in which reservoir contents are stored. MEMS methods, micromolding, and micromachining techniques known in the art can be used to fabricate the substrate/reservoirs from a variety of materials. See, for example, U.S. Pat. No. 6,123,861 and U.S. patent application Publication No. 2002/0107470. Examples of suitable substrate materials include silicon, metals, ceramics, semiconductors, and degradable and non-degradable polymers. In one embodiment, the substrate serves as the support or base for a drug delivery or biosensing microchip.

The substrate can have a variety of shapes, or shaped surfaces. The substrate may consist of only one material, or may be a composite or multi-laminate material, that is, composed of several layers of the same or different substrate materials that are bonded together. Preferably, the substrate is hermetic, that is impermeable (at least during the time of use of the reservoir device) to the molecules to be delivered and to surrounding gases or fluids (e.g., water, blood, electrolytes or other solutions).

The substrate thickness can vary. For example, the thickness of a device may vary from approximately 10 μm to several millimeters (e.g., 500 μm). Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of drug formulation needed for a particular application, although other constraints such as manufacturing limitations or total device size limitations (e.g., for implantation into a patient) also may come into play. For example, devices for in vivo applications desirably would be small enough to be implanted using minimally invasive procedures.

The substrate includes at least two and preferably tens or hundreds of reservoirs. For example, one reservoir could be provided for each daily dose of drug required, for example, over a 3-, 8-, or 12-month course of treatment. The substrate could include, for example, 300 to 400 reservoirs.

In one embodiment, the reservoir has a volume equal to or less than 500 μL (e.g., less than 250 μL, less than 100 μL, less than 50 μL, less than 25 μL, less than 10 μL, etc.) and greater than about 1 nL (e.g., greater than 5 nL, greater than 10 nL, greater than about 25 nL, greater than about 50 nL, greater than about 1 μL, etc.).

Reservoir Contents

The reservoir contents are essentially any object or material that needs to be isolated (e.g., protected from) the environment outside of the reservoir until a selected point in time, when its release or exposure is desired. In various embodiments, the reservoir contents comprise (a quantity of) molecules, a secondary device, or a combination thereof. Proper functioning of certain reservoir contents, such as a catalyst or sensor, generally does not require release from the reservoir; rather their intended function, e.g., catalysis or sensing, occurs upon exposure of the reservoir contents to the environment outside of the reservoir after opening of the reservoir cap. Thus, the catalyst molecules or sensing component can be released or can remain immobilized within the open reservoir. Other reservoir contents such as drug molecules often may need to be released from the reservoir in order to pass from the device and be delivered to a site in vivo to exert a therapeutic effect on a patient. However, the drug molecules may be retained for certain in vitro applications.

Molecules

The reservoir contents can include essentially any natural or synthetic, organic or inorganic molecule or mixture thereof. The molecules may be in essentially any form, such as a pure solid or liquid, a gel or hydrogel, a solution, an emulsion, a slurry, or a suspension. The molecules of interest may be mixed with other materials to control or enhance the rate and/or time of release from an opened reservoir. In various embodiments, the molecules may be in the form of solid mixtures, including amorphous and crystalline mixed powders, monolithic solid mixtures, lyophilized powders, and solid interpenetrating networks. In other embodiments, the molecules are in liquid-comprising forms, such as solutions, emulsions, colloidal suspensions, slurries, or gel mixtures such as hydrogels.

For in vivo applications, the chemical molecule can be a therapeutic, prophylactic, or diagnostic agent. As used herein, the term "drug" includes any therapeutic or prophylactic agent (e.g., an active ingredient). The drug can comprise small molecules, large (i.e., macro-) molecules, or a combination thereof, having a bioactive effect. In one embodiment, the large molecule drug is a protein or a peptide. In various other embodiments, the drug can be selected from amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants (e.g., LMWH, pentasaccharides), antibiotics (e.g., immunosuppressants), analgesic agents, and vitamins. In one embodiment, the drug is a protein. Examples of suitable types of proteins include, glycoproteins, enzymes (e.g., proteolytic enzymes), hormones or other analogs (e.g., LHRH, steroids, corticosteroids, growth factors), antibodies (e.g., anti-VEGF antibodies, tumor necrosis factor inhibitors), cytokines (e.g., $\alpha$-, $\beta$-, or $\gamma$-interferons), interleukins (e.g., IL-2, IL-10), and diabetes/obesity-related therapeutics (e.g., insulin, exenatide, PYY, GLP-1 and its analogs). In one embodiment, the drug is a gonadotropin-releasing (LHRH) hormone analog, such as leuprolide. In another exemplary embodiment, the drug comprises parathyroid hormone, such as a human parathyroid hormone or its analogs, e.g., hPTH(1-84) or hPTH(1-34). In a further embodiment, the drug is selected from nucleosides, nucleotides, and analogs and conjugates thereof. In yet another embodiment, the drug comprises a peptide with natriuretic activity, such as atrial natriuretic peptide (ANP), B-type (or brain) natriuretic peptide (BNP), C-type natriuretic peptide (CNP), or dendroaspis natriuretic peptide (DNP). In still another embodiment, the drug is selected from diuretics, vasodilators, inotropic agents, anti-arrhythmic agents, $Ca^+$ channel blocking agents, anti-adrenergics/sympatholytics, and renin angiotensin system antagonists. In one embodiment, the drug is a VEGF inhibitor, VEGF antibody, VEGF antibody fragment, or another anti-angiogenic agent. Examples include an aptamer, such as MACUGEN™ (Pfizer/ Eyetech) (pegaptanib sodium)) or LUCENTIS™ (Genetech/ Novartis) (rhuFab VEGF, or ranibizumab), which could be used in the prevention of choroidal neovascularization. In yet a further embodiment, the drug is a prostaglandin, a prostacyclin, or another drug effective in the treatment of peripheral vascular disease. In various other embodiments, the drug is selected from tumor necrosis factors (TNF), TNF antagonists (e.g., ENBREL™), angiogenic agents (e.g., VEGF), and anti-inflammatory agents (e.g., dexamethasone).

In one embodiment, a device is used to deliver a drug systemically to a patient in need thereof In another embodiment, the construction and placement of the microchip in a patient enables the local or regional release of drugs that may be too potent for systemic delivery of an effective dose. The reservoir contents in one reservoir or in one device can include a single drug or a combination of two or more drugs, and the reservoir contents can further include pharmaceutically acceptable carriers.

The molecules can be provided as part of a "release system," as taught in U.S. Pat. No. 5,797,898, the degradation, dissolution, or diffusion properties of which can provide a method for controlling the release rate of the molecules. The release system may include one or more pharmaceutical excipients. Suitable pharmaceutically acceptable excipients include most carriers approved for parenteral administration, including various aqueous solutions (e.g., saline, Ringer's, Hank's, and solutions of glucose, lactose, dextrose, ethanol, glycerol, albumin, and the like). Examples of other excipients and diluents include calcium carbonate and sugars. Other excipients may be used to maintain the drug in suspensions as an aid to reservoir filling, stability, or release. Depending on the properties of the drug, such excipients may be aqueous or non-aqueous, hydrophobic or hydrophilic, polar or non-polar, protic or aprotic. Such excipients generally have low reactivity. See. e.g., U.S. Pat. No. 6,264,990 to Knepp et al. The release system optionally includes stabilizers, antioxidants, antimicrobials, preservatives, buffering agents, surfactants, and other additives useful for storing and releasing molecules from the reservoirs in vivo.

The release system may provide a more continuous or consistent release profile (e.g., pulsatile) or constant plasma level as needed to enhance a therapeutic effect, for example. Pulsatile release can be achieved from an individual reservoir, from a plurality of reservoirs, or a combination thereof. For example, where each reservoir provides only a single pulse, multiple pulses (i.e. pulsatile release) are achieved by temporally staggering the single pulse release from each of several reservoirs. Alternatively, multiple pulses can be achieved from a single reservoir by incorporating several layers of a release system and other materials into a single reservoir. Continuous release can be achieved by incorporating a release system that degrades, dissolves, or allows diffusion of molecules through it over an extended period. In addition, continuous release can be approximated by releasing several pulses of molecules in rapid succession ("digital" release, analogous to the digital storage and reproduction of music). The active release systems described herein can be used alone or on combination with passive release systems known in the art, for example, as described in U.S. Pat. No. 5,797,898. For example, the reservoir cap can be removed by electrothermal ablation as described herein to expose a passive release system that only begins its passive release after the reservoir cap has been actively removed. Alternatively, a given substrate can include both passive and active release reservoirs.

For in vitro applications, the molecules can be any of a wide range of molecules where the controlled release of a small (milligram to nanogram) amount of one or more molecules is required, for example, in the fields of analytic chemistry or medical diagnostics. Molecules can be effective as pH buffering agents, diagnostic reagents, and reagents in complex reactions such as the polymerase chain reaction or other nucleic acid amplification procedures. In various other embodiments, the molecules to be released are fragrances or scents, dyes or other coloring agents, sweeteners or other concentrated flavoring agents, or a variety of other compounds. In yet other embodiments, the reservoirs contain immobilized molecules. Examples include any chemical species which can be involved in a reaction, including reagents, catalysts (e.g., enzymes, metals, and zeolites), proteins, nucleic acids, polysaccharides, cells, and polymers, as well as organic or inorganic molecules which can function as a diagnostic agent.

Secondary Devices

As used herein, unless explicitly indicated otherwise, the term "secondary device" includes any device or a component thereof which can be located in a reservoir. In one embodiment, the secondary device is a sensor or sensing component thereof. As used herein, a "sensing component" includes a component utilized in measuring or analyzing the presence, absence, or change in a chemical or ionic species, energy, or one or more physical properties (e.g., pH, pressure) at a site. Types of sensors include biosensors, chemical sensors, physical sensors, or optical sensors. Examples of biosensors that could be adapted for use in/with the reservoir devices described herein include those taught in U.S. Pat. No. 6,486, 588; U.S. Pat. No. 6,475,170; and U.S. Pat. No. 6,237,398. Secondary devices are further described in U.S. Pat. No. 6,551,838.

Examples of sensing components include components utilized in measuring or analyzing the presence, absence, or change in a drug, chemical, or ionic species, energy (or light), or one or more physical properties (e.g., pH, pressure) at a site. In one embodiment, a device is provided for implantation in a patient (e.g., a human or other mammal) and the reservoir contents comprises at least one sensor indicative of a physiological condition in the patient. For example, the sensor could monitor the concentration of glucose, urea, calcium, or a hormone present in the blood, plasma, interstitial fluid, or other bodily fluid of the patient.

In one embodiment, the device includes one or more MEMS gyroscopes, attached to or integrated into the device, e.g., on or in a substrate portion. For example, the gyro could be employed in a sensor application, e.g., telematics or biomechanics.

Several options exist for receiving and analyzing data obtained with secondary devices located within the primary device, which can be a microchip device or another device. Devices may be controlled by local microprocessors or remote control. Biosensor information may provide input to the controller to determine the time and type of activation automatically, with human intervention, or a combination thereof. For example, the operation of an implantable drug delivery system (or other controlled release/controlled reservoir exposure system) can be controlled by an on-board microprocessor (i.e., within the package of the implantable device). The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the implantable device. Power can be supplied to the implantable device locally by a battery or remotely by wireless transmission. See, e.g., U.S. patent application Publication No. 2002/0072784.

In one embodiment, a device is provided having reservoir contents that include drug molecules for release and a sensor/sensing component. For example, the sensor or sensing component can be located in a reservoir or can be attached to the device substrate. The sensor can operably communicate with the device, e.g., through a microprocessor, to control or modify the drug release variables, including dosage amount and frequency, time of release, effective rate of release, selection of drug or drug combination, and the like. The sensor or sensing component detects (or not) the species or property at the site of in vivo implantation and further may relay a signal to the microprocessor used for controlling release from the device. Such a signal could provide feedback on and/or finely control the release of a drug. In another embodiment, the device includes one or more biosensors (which may be sealed in reservoirs until needed for use) that are capable of detecting and/or measuring signals within the body of a patient.

As used herein, the term "biosensor" includes sensing devices that transduce the chemical potential of an analyte of interest into an electrical signal, as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

Reservoir Caps

As used herein, the term "reservoir cap" includes a membrane or other structure suitable for separating the contents of a reservoir from the environment outside of the reservoir. It generally is self-supporting across the reservoir opening, although caps having additional structures to provide mechanical support to the cap can be fabricated. Selectively removing the reservoir cap or making it permeable will then "expose" the contents of the reservoir to the environment (or selected components thereof) surrounding the reservoir. In preferred embodiments, the reservoir cap is selectively disintegrated. As used herein, the term "disintegrate" is used broadly to include without limitation degrading, dissolving, rupturing, fracturing or some other form of mechanical failure, as well as a loss of structural integrity due to a chemical reaction (e.g., electrochemical degradation) or phase change (e.g., melting) in response to a change in temperature, unless a specific one of these mechanisms is indicated. In one specific embodiment, the "disintegration" is by an electrochemical activation technique, such as described in U.S. Pat. No. 5,797,898. In another specific embodiment, the "disintegration" is by an electro-thermal ablation technique, such as described in U.S. patent application Publication No. 2004/0121486 A1 to Uhland, et al. In the latter technique, the reservoir cap is formed of a conductive material, such as a metal film, through which an electrical current can be passed to electrothermally ablate it, as described in U.S. patent application Publication No. 2004/0121486 A1 to Uhland, et al. Representative examples of suitable reservoir cap materials include gold, copper, aluminum, silver, platinum, titanium, palladium, various alloys (e.g., Au/Si, Au/Ge, Pt—Ir, Ni—Ti, Pt—Si, SS 304, SS 316), and silicon doped with an impurity to increase electrical conductivity, as known in the art. In one embodiment, the reservoir cap is in the form of a thin metal film. In one embodiment, the reservoir cap is part of a multiple layer structure, for example, the reservoir cap can be made of multiple metal layers, such as a multi-layer/laminate structure of platinum/titanium/platinum. The reservoir cap is operably (i.e., electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated (i.e., ruptured/disintegrated).

In another embodiment, multiple reservoir caps may be located over an individual reservoir and supported by a grid structure, as described in U.S. Patent Application No. 60/606,387, which is incorporated herein by reference. Such multiple caps allow a larger area of the reservoir to be exposed than may be feasible using a single large cap. For example, opening a large cap may require more power or generation of more heat that could damage tissue or sensors compared to opening several smaller caps. Smaller caps may be opened simultaneously or sequentially.

Means for Controlling Reservoir Opening

The multi-reservoir device includes a control means to control the time at which the reservoir cap is disintegrated to release or expose the reservoir contents (e.g., to initiate drug release from the device and into the patient's body, or to permit sensor exposure in vivo).

In one embodiment, the means for controllably releasing the drug provides selective actuation of each reservoir, which is done under the control of a microprocessor. Preferably, such means includes an input source, a microprocessor, a timer, a demultiplexer (or multiplexer), and a power source. As used herein, the term "demultiplexer" also refers to multiplexers. The power source provides energy to activate the selected reservoir, i.e., trigger release of drug from the particular reservoir desired for a given dose. The microprocessor can be programmed to initiate the disintegration or permeabilization of the reservoir cap in response at a pre-selected time or in response to one or more of signals or measured parameters, including receipt of a signal from another device (for example by remote control or wireless methods) or detection of a particular condition using a sensor such as a biosensor.

The medical device can also be activated or powered using wireless means, for example, as described in U.S. 20020072784 A1 to Sheppard et al.

In one embodiment, the medical device includes a substrate having a two-dimensional array of reservoirs arranged therein, a release system comprising drug contained in the reservoirs, anode reservoir caps covering each of the reservoirs, cathodes positioned on the substrate near the anodes, and means for actively controlling disintegration of the reservoir caps. The energy drives a reaction between selected anodes and cathodes. Upon application of a small potential between the electrodes, electrons pass from the anode to the cathode through the external circuit causing the anode material (reservoir cap) to oxidize and dissolve into the surrounding fluids, exposing the release system containing the drug for delivery to the surrounding fluids, e.g., in vivo. For example, the microprocessor can direct power to specific electrode pairs through a demultiplexer as directed by an EPROM, remote control, or biosensor.

In another embodiment, the activation energy initiates a thermally driven rupturing or permeabilization process, for example, as described in U.S. Pat. No. 6,527,762. For example, the means for controlling release can actively disintegrate or permeabilize a reservoir cap using a resistive heater. The resistive heater can cause the reservoir cap to undergo a phase change or fracture, for example, as a result of thermal expansion of the reservoir cap or release system, thereby rupturing the reservoir cap and releasing the drug from the selected reservoir. The application of electric current to the resistive heater can be delivered and controlled using components as described above for use in the electrochemical disintegration embodiment. For example, a microprocessor can direct current to select reservoirs at desired intervals.

In yet another embodiment, control means controls electro-thermal ablation of the reservoir cap. For example, the drug delivery device could include a reservoir cap formed of an electrically conductive material, which prevents the reservoir contents from passing out from the device; an electrical input lead connected to the reservoir cap; an electrical output lead connected to the reservoir cap; and a control means to deliver an effective amount of electrical current through the reservoir cap, via the input lead and output lead, to heat and rupture the reservoir cap to release the drug. In one embodiment, the reservoir cap and conductive leads are formed of the same material, where the temperature of the reservoir cap increases locally under applied current because the reservoir cap is suspended in a medium that is less thermally conductive than the substrate. Alternatively, the reservoir cap and conductive leads are formed of the same material, and the reservoir cap has a smaller cross-sectional area in the direction of electric current flow, where the increase in current density through the reservoir cap causes an increase in localized heating. The reservoir cap alternatively can be formed of a material that is different from the material forming the leads, wherein the material forming the reservoir cap has a different electrical resistivity, thermal diffusivity, thermal conductivity, and/or a lower melting temperature than the material forming the leads. Various combinations of these embodiments can be employed as described in U.S. patent application Publication No. 2004/0121486 A1 to Uhland, et al.

In one embodiment, the drug delivery device utilizes an accelerated release mechanism. In one embodiment, a positive displacement feature can be included to facilitate release of the drug from the reservoirs. For example, the device may include an osmotic engine or water-swellable component, which can be used to drive a drug formulation from the reservoirs. For example, such a feature can provide very fast release of drug the efficacy of which is dependent on a fast pharmacokinetic pulsatile profile. As used herein, the term "accelerated release" refers to an increase in the transport rate of drug out of the reservoir relative to the transport rate of the drug solely by diffusion down its own chemical gradient. The terms also refer to expelling reservoir contents that would not otherwise egress from an open reservoir, i.e., where no or negligible diffusion could occur.

Operation and Use of the Devices

The devices made by the methods described herein can be used in a wide variety of applications. Preferred applications include the controlled delivery of a drug, biosensing, or a combination thereof. Embodiments for some of these applications are described below.

In one embodiment, a microchip device is provided for implantation into a patient, such as a human or other vertebrate animal, for controlled drug delivery. In one embodiment, the microchip device can be implanted in vivo using standard surgical or minimally-invasive implantation techniques. Such microchip devices are especially useful for drug therapies in which one needs to very precisely control the exact amount, rate, and/or time of delivery of the drug. Exemplary drug delivery applications include the delivery of potent molecules, including, hormones (e.g., PTH), steroids, cytokines, chemotherapeutics, vaccines, gene delivery vectors, anti-VEGF aptamers, and certain analgesic agents.

In other embodiments, the device described herein is incorporated into a variety of other types and designs of implantable medical devices, such as the cardiac sensing and neurostimulation. In another example, it could be incorporated into another medical device, in which the present devices and systems release drug into a carrier fluid that then flows to a desired site of administration, as illustrated for example in U.S. Pat. No. 6,491,666.

The devices also have numerous in vivo, in vitro, and commercial diagnostic applications. The devices are capable of delivering precisely metered quantities of molecules and thus are useful for in vitro applications, such as analytical chemistry, drug discovery, and medical diagnostics, as well as biological applications such as the delivery of factors to cell cultures. In still other non-medical applications, the devices are used to control release of fragrances, dyes, or other useful chemicals. Other methods of using the devices for controlled release of molecules, as well as for controlled exposure or release of secondary devices, are described in U.S. Pat. No. 5,797,898; U.S. Pat. No. 6,123,861; U.S. Pat. No. 6,527,762; U.S. Pat. No. 6,491,666; U.S. Pat. No. 6,551,838 and U.S. patent application Publications No. 2002/0072784; No. 2002/0107470; No. 2002/0151776; No. 2002/0099359; and No. 2003/0010808.

Patents and publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method for making a multi-reservoir device comprising:
    patterning one or more photoresist layers on a substrate;
    depositing onto the substrate at least one metal layer by physical vapor deposition;
    forming a plurality of reservoir caps and conductive traces from the at least one metal layer by using the one or more photoresist layers in a liftoff process or wet chemical etching such that each reservoir cap is electrically connected to two conductive traces;
    removing the one or more photoresist layers using a liftoff process;
    forming a plurality of reservoirs in the substrate;
    loading each reservoir with reservoir contents; and
    sealing each reservoir.

2. The method of claim 1, wherein the reservoir cap comprises a first conductive metal layer coated with one or more protective noble metal film layers.

3. The method of claim 2, wherein the first conductive metal layer comprises titanium.

4. The method of claim 2, wherein the noble metal film comprises platinum.

5. The method of claim 2, wherein the thickness of the protective metal layer is less than about 20% of the thickness of the first conductive metal layer.

6. The method of claim 1, wherein the reservoirs comprise interior sidewalls and the method further includes forming at least one protective layer of material onto the sidewalls.

7. The method of claim 6, wherein the layer covering the sidewalls comprise a material selected from the group consisting of gold, platinum, diamond-like carbon, silicon carbide, silicon dioxide, and platinum silicide.

8. The method of claim 1, wherein the reservoirs comprise interior sidewalls comprising silicon doped with boron or another impurity to enhance the resistance of the silicon to etching under in vivo conditions.

9. The method of claim 1, further comprising bonding an additional substrate portion with through-substrate holes aligned with the reservoirs.

10. The method of claim 9, wherein the additional substrate portion comprises a silicon wafer or a glass wafer.

11. The method of claim 9, wherein the substrate and/or the additional substrate portion comprises silicon and the reservoirs and/or through holes are further treated with an isotropic silicon etchant to widen the hole or to smooth the surface of the hole.

12. The method of claim 9, wherein the additional substrate portion and the substrate are bonded together with an intermediate film.

13. The method of claim 12, wherein the intermediate film comprises a borosilicate glass.

14. The method of claim 9, wherein the additional substrate portion and the substrate are bonded by a process comprising anodic bonding, thermocompression bonding, or eutectic bonding.

15. The method of claim 1, comprising a bilayer liftoff process.

16. The method of claim 15, wherein the bilayer photoresist comprises an upper layer and a lower layer, wherein the lower layer is disposed on the substrate and the upper layer is disposed on the lower layer.

17. The method of claim 15, wherein the metal layer has no tags created by the sputtering and liftoff processes.

18. The method of claim 17, wherein the lower layer is laterally etched before the sputtering step, to create an overhang of the upper layer so that substantially no sputtered material is deposited on the sidewall of the lower layer.

19. The method of claim 15, wherein tags connected to the metal layer are formed by the sputtering and liftoff processes, and the tags are then removed.

20. The method of claim 19, wherein the tags are removed by a process comprising:
depositing a mask layer is deposited over the metal traces and/or reservoir caps, wherein the mask layer:metal layer thickness ratio is from about 1:5 to about 1:1000; and
etching away the tags to yield metal traces and/or reservoir caps.

21. The method of claim 19, wherein the tags are removed by a sonication process.

22. A microfabrication method comprising:
patterning a bilayer of photoresist on a substrate, wherein the bilayer photoresist comprises an upper layer and a lower layer, the lower layer being disposed on top of the substrate and the upper layer being disposed on top of the lower layer;
etching the lower layer away in select areas to form one or more bridges comprising areas of the upper layer over and spaced apart from the substrate, each said bridge having opposing first and second connection regions that are connected to the substrate;
depositing onto the substrate at least one metal layer by physical vapor deposition, wherein the one or more bridges provide a shielding effect to produce a metal film or patterned metal feature with a thickness variation within a single metal layer, without etching the metal layer;
forming a plurality of reservoir caps and conductive traces from the at least one metal layer by using the one or more photoresist layers in a liftoff process or wet chemical etching such that each reservoir cap is electrically connected to two conductive traces;
removing the bilayer photoresist layers using a liftoff process;
forming a plurality of reservoirs in the substrate;
loading each reservoir with reservoir contents; and
sealing each reservoir.

23. The method of claim 22, wherein the deposition method is selected from evaporation, sputtering, or ion beam deposition.

24. A method for making a multi-reservoir device comprising:
depositing a layer of a nitride material on a silicon substrate;
patterning the nitride layer with photoresist;
etching the nitride layer using an RIE process;
stripping off the photoresist;
anistropically etching the silicon substrate;
forming metal traces by depositing and patterning a first metal layer;
forming reservoir caps by depositing and patterning a second metal layer atop
portions of the first metal layer using a liftoff technique to form a structure;
applying a passivation layer onto the structure;
etching the passivation layer; and
etching the nitride layer from under the reservoir cap.

25. The method of claim 24, further comprising anodically bonding a patterned glass wafer to the substrate.

26. The method of claim 1, wherein the reservoirs are micro-reservoirs.

27. The method of claim 1, wherein the reservoir contents comprises one or more drugs.

28. The method of claim 1, wherein the reservoir contents comprises one or more sensors or sensor components.

29. The method of claim 1, wherein the reservoir contents are hermetically sealed within the reservoirs.

30. The method of claim 1, wherein respective said conductive traces are connected to respective said reservoir caps and formed from the same one metal layer.

31. The method of claim 24, wherein said step of forming metal traces by depositing and patterning the first metal layer uses a liftoff technique.

32. The method of claim 24, wherein said step of forming metal traces by depositing and patterning the first metal layer uses a liquid etchant.

* * * * *